United States Patent [19]

Chafin et al.

[11] Patent Number: 5,073,656

[45] Date of Patent: Dec. 17, 1991

[54] HIGH ETHYLENE TO ETHANE PROCESSES FOR OXIDATIVE COUPLING

[75] Inventors: Richard B. Chafin, Hurricane; Barbara K. Warren, Charleston, both of W. Va.

[73] Assignee: Union Carbide Chemicals and Plastics Company, Inc., Danbury, Conn.

[21] Appl. No.: 409,544

[22] Filed: Sep. 19, 1989

[51] Int. Cl.$^5$ .................................................. C07C 2/00
[52] U.S. Cl. .................................. 585/500; 585/657; 585/658; 585/700; 585/943
[58] Field of Search ............... 585/500, 657, 658, 943, 585/700

[56] References Cited

U.S. PATENT DOCUMENTS

| | | |
|---|---|---|
| 4,172,810 | 10/1979 | Mitchell et al. . |
| 4,465,893 | 8/1984 | Olah ................................... 585/709 |
| 4,544,784 | 10/1985 | Sofranko et al. .................... 585/400 |
| 4,634,800 | 1/1987 | Withers, Jr. et al. ............... 585/658 |
| 4,654,459 | 3/1987 | Sofranko ............................. 585/500 |
| 4,654,460 | 3/1987 | Kimble et al. . |
| 4,658,077 | 4/1987 | Kolts et al. ......................... 585/418 |
| 4,795,842 | 1/1989 | Gaffney et al. ..................... 585/654 |

FOREIGN PATENT DOCUMENTS 52925 2/1986 Australia .
0198251 10/1986 European Pat. Off. ............ 585/500

OTHER PUBLICATIONS

Chemical Abstracts, vol. 108, No. 21, May 1988, Abstract 186163 g.
Matsuhashi et al., "Formation of $C_3$ Hydrocarbons from Methane Catalyzed by $Na^+$ Doped $ZrO_2$", Chem. Soc. Japan, Chem. Lett. 585 (1989).
Fujimoto et al., "Selective Oxidative Coupling of Methane Over Supported Alkaline Earth Metal Halide Catalysts", Appl. Catal., vol. 50, 223 (1989).

Primary Examiner—Patrick P. Garvin
Assistant Examiner—E. D. Irzinski
Attorney, Agent, or Firm—Jean B. Mauro

[57] ABSTRACT

Oxidative coupling of lower alkane to higher hydrocarbon is conducted using catalyst comprising barium and/or strontium component and a metal oxide combustion promoter in the presence of vapor phase halogen component. High ethylene to ethane mole ratios in the product can be obtained over extended operating periods.

29 Claims, No Drawings

HIGH ETHYLENE TO ETHANE PROCESSES FOR OXIDATIVE COUPLING

This invention was made under United States of America Government support under Contract No. DE-AC22-87PC79817 awarded by the Department of Energy. The Government has certain rights in this invention.

RELATED APPLICATIONS

U.S. patent application Ser. No. 463,320, filed Jan 10, 1990; U.S. patent application Ser. No. 542,699, filed June 25, 1990; U.S. patent application Ser. No. 543,393, filed June 26, 1990; all of which are commonly assigned.

The following are related, commonly assigned applications, filed on an even date herewith:
U.S. patent application Ser. No. 409,361; U.S. patent application Ser. No. 409,375; U.S. patent application Ser. No. 409,376; U.S. patent application Ser. No. 409,369; and U.S. patent application Ser. No. 409,359.

This invention relates to processes for the oxidative coupling of methane to higher molecular weight hydrocarbon wherein high ratios of ethylene to ethane are produced.

BACKGROUND OF THE INVENTION

Processes for the conversion of lower molecular weight alkanes such as methane to higher molecular weight hydrocarbons which have greater value are sought. One of the proposals for the conversion of lower molecular weight alkanes is by oxidative coupling For instance, G. E. Keller and M. M. Bhasin disclose in *Journal of Catalysis*, Volume 73, pages 9 to 19 (1982) that methane can be converted to, e.g., ethylene The publication by Keller, et al., has preceded the advent of substantial patent and open literature disclosures by numerous researchers pertaining to processes for the oxidative coupling of lower alkanes and catalysts for such processes.

In order for an oxidative coupling process to be commercially attractive, the process should be capable of providing a good rate of conversion of the lower alkanes with high selectivity to the sought higher molecular weight hydrocarbons. Since conversion and selectivity can be enhanced by catalysts, catalytic processes have been the thrust of work done by researchers in oxidative coupling.

Two general types of oxidative coupling processes are the sequential, or pulsed, processes and the cofeed processes. The sequential processes are characterized by alternately cycling an oxygen-containing gas and an alkane-containing gas for contact with a catalyst. These processes typically provide high selectivities to higher hydrocarbon but suffer from operational complexities in cycling the catalyst environment and in the tendency of the processes to produce less desirable, higher molecular weight products and to have carbonaceous deposits form on the catalyst, thereby necessitating regeneration. Thus, from an operational standpoint, cofeed processes, i.e., processes in which oxygen-containing material and alkane are simultaneously fed to the reaction zone containing the catalyst, are more desirable.

In order for cofeed processes to be commercially attractive, especially for the production of large volume commodity chemicals such as ethylene and ethane ($C_2$'s), not only must the conversion of alkane be high and the selectivity to higher hydrocarbons as opposed to combustion products such as carbon dioxide and carbon monoxide be high, but also, the catalyst must exhibit a relatively long lifetime with the high performance. Moreover, because of the value of ethylene, processes in which the $C_2$'s produced are rich in ethylene are sought.

Numerous catalysts have been proposed by researchers for oxidative coupling processes. These catalyst have included catalysts containing alkali and/or alkaline earth metals. The alkali and alkaline earth metals have been suggested as being in the oxide, carbonate and halide forms. Other components such as rhenium, tungsten, copper, bismith, lead, tin, iron, nickel, zinc, indium, vanadium, palladium, platinum, iridium, uranium, osmium, rhodium, zirconium, titanium, lanthanum, aluminum, chromium, cobalt, beryllium, germanium, antimony, gallium, manganese, yttrium, cerium, praseodymium (and other rare earth oxides), scandium, molybdenum, thallium, thorium, cadmium, boron, among other components, have also been suggested for use in oxidative coupling catalysts. See, for instance, U.S. Pat. Nos. 4,450,310; 4,443,646; 4,499,324; 4,443,645; 4,443,648; 4,172,810; 4,205,194; 4,239,658; 4,523,050; 4,443,647; 4,499,323; 4,443,644; 4,444,984; 4,695,668; 4,704,487; 4,777,313; 4,780,449; International Patent Publication WO 86/07351, European Patent Application Publications Nos. 189079 (1986); 206042 (1986); 206044 (1986), and 177327 (1985), Australian Patent No. 52925 (1986), Moriyama, et al., "Oxidative Dimerization of Methane Over Promoted MgO, Important Factors," Chem. Soc. Japan, Chem. Lett., 1165 (1986), and Emesh, et al., "Oxidative Coupling of Methane over the Oxides of Groups IIIA, IVA and VA Metals," J. Phys. Chem, Vol. 90, 4785 (1986).

Several researchers have proposed the use of alkali or alkaline earth metals in the form of halides (e.g., chloride, bromide or iodide) in oxidative coupling catalysts. Australian Patent No. 52925 discloses the use of supported calcium chloride, barium bromide, potassium iodide, lithium chloride, cesium chloride, among others for catalysts to oxidatively couple methane to ethane and ethylene. The catalysts are supported. The patent application states at page 5

"The chloride, bromide and iodide catalysts are preferably employed on a support consisting of pumice-stone, silica gel, kieselghur, precipitated silica and/or oxides of the alkaline earth elements and/or aluminum oxide, silicon dioxide, zinc oxide, titanium dioxide, zirconium dioxide and/or silicon carbide. Of the oxides of alkaline earth elements which are employed as a support, magnesium oxide and calcium oxide are preferred."

The patentees disclose feeding hydrogen halide to the reaction zone. None of the reported examples use the addition of hydrogen halide. Also, the patentees did not report the time on stream of the catalyst when the conversion values are determined. Metal halide catalysts often decompose upon initiation of the process. This produces an initial unsteady state operation in which exceptionally high selectivities to $C_2$'s and high ethylene to ethane ratios occur. These exceptionally high selectivities and ratios have been found by us often to be fleeting. See also the corresponding German patent application 3,503,664. Included within the examples are illustrations of the use of, e.g., $CaCl_2$ on pumice, $CaCl_2$-$MgCl_2$ on pumice, $BaBr$ on pumice, $CaI_2$ on pumice, BaBr$_2$ on calcium oxide, CaBr$_2$ on magnesia, BaBr$_2$ on silicon carbide, KBr on titanium dioxide, and BaBr$_2$ on zinc oxide.

The deactivation of oxidation coupling catalysts through the loss of components via vaporization of halide compounds under the high temperatures of oxidative coupling has been opined by Fujimoto, et al., "Oxidative Coupling of Methane with Alkaline Earth Halide Catalysts Supported on Alkaline Earth Oxide", Chem. Soc. Japan, Chem. Lett., 2157 (1987). Catalysts exemplified include MgCl$_2$ on titania, MgF$_2$ on magnesia, MgCl$_2$ on magnesia, CaCl$_2$ on magnesia, MgCl$_2$ on calcium oxide, CaF$_2$ on calcium oxide, CaBr$_2$ on calcium oxide, MgCl$_2$ on silica, MgBr$_2$ on magnesia, CaBr on magnesia, MgBr$_2$ on calcium oxide and CaCl$_2$ on calcium oxide. The authors conclude "Unsupported MgO exhibits poor catalytic properties for oxidative coupling of methane while CaO is highly reactive for the reaction. Both of them are comparably active and selective for the reaction when they are impregnated with chloride of magnesium or calcium. However, MgCl$_2$ on other supports such as TiO$_2$ or SiO$_2$, exhibit much poorer catalytic functions than CaO or MgO supported ones."

European Patent Application 210 383 (1986) discloses the addition of gas phase material containing halogen component such as chlorine, methyl chloride and methyl dichloride. Enhanced selectivities are reported when the halogen component is present. The catalysts include those containing one or more of alkali and alkaline earth metal, alkali metal with lanthanide oxide, zinc oxide, titanium oxide or zirconium oxide, and others. In the examples on page 28, a comparison is made between a Li$_2$O/MgO (with and without halide addition) to a Li$_2$O/TiO$_2$ (with and without halide addition). In both, the ratio of ethylene to ethane was enhanced by the addition of halide (to a greater extent with the Li$_2$O/TiO$_2$ catalyst), but only the Li$_2$O/MgO catalyst appeared to have increased in activity with the presence of halide.

U.S. Pat. No. 4,654,460 discloses the addition of a halogen-containing material either in the catalyst or via a feed gas in an oxidative coupling process. The catalyst contains one or more alkali metal and alkaline earth metal components. Although no working examples are provided illustrating the effect of halide additions, conversions of methane are said to be increased with halides and selectivities to higher hydrocarbons, particularly ethylene, improved. See also, Burch, et al., "Role of Chlorine in Improving Selectivity in the Oxidative Coupling of Methane to Ethylene", Appl. Catal., Vol. 46, 69 (1989) and "The Importance of Heterogeneous and Homogeneous Reactions in Oxidative Coupling of Methane Over Chloride Promoted Oxide Catalysts," Catal. Lett., vol. 2, 249 (1989), who propose mechanistic possibilities for the effect of halide in oxidative coupling of methane, and Minachev, et al., "Oxidative Condensations of Methane—a New Pathway to the Synthesis of Ethane, Ethylene, and Other Hydrocarbons", Russ. Chem. Rev., Vol. 57, 221 (1988).

Barium-containing catalysts for oxidative coupling have been proposed by, for instance, Yamagata, et al., "Oxidative Coupling of Methane over BaO Mixed with CaO and MgO," Chem. Soc. Japan, Chem. Lett., 81 (1987) (catalysts include BaO/MgO, BaO/Al$_2$O$_3$, BaO/CaO, BaO/ZrO$_2$ and BaO/TiO$_2$). The authors conclude that the BaO/MgO and BaO/CaO catalysts are much more effective than BaO on other supports such as titania, zirconia, alumina, silica and ferric oxide. They said that XRD analyses suggest the formation of some mixed compounds, probably the mixed oxides or the mixed carbonates, together with BaCO$_3$. Aika, et al., "Oxidative Dimerization of Methane over BaCO$_3$, SrCO$_3$ and these Catalysts Promoted with Alkali", J. Chem. Soc., Chem. Comm. 1210 (1986) (catalysts exemplified include BaCO$_3$, BaO, SrCO$_3$, TiO$_2$, ZrO$_2$) relate that TiO$_2$ and ZrO$_2$ are not good catalysts. See also, International Patent Application WO 86/7351, (BaO/La$_2$O$_3$, BaO/MgO); U S. Pat. Nos. 4,172,810 (Ba-Cr-Pt/MgAl$_2$O$_4$, sequential process), 4,704,487, 4,704,488, and 4,709,108 (BaO/Al$_2$O$_3$, zirconia, titania components); Nagamoto, et al., "Methane Oxidation over Perovskite-Type Oxide Containing Alkaline Earth Metal", Chem. Soc. Japan, Chem. Lett., 237 (1988), (SrZrO$_3$, BaTiO$_3$); Otsuka, et al., "Peroxide Anions as Possible Active Species in Oxidative Coupling of Methane", Chem. Soc. Japan, Chem. Lett., 77 (1987) (Strontium peroxide and barium peroxide mechanisms); Roos, et al., "Selective Oxidation of Methane to Ethane and Ethylene Over Various Oxide catalysts", Catal. Today, Vol. 1, 133 (1987), (Ca/Al$_2$O$_3$); Iwamatsu, et al., "Importance of the Specific Surface Area in Oxidative Dimerization of Methane over Promoted MgO", J. Chem. Soc., Chem. Comm., 19 (1987), (Sr/MgO, Ca/MgO, Ba/MgO); Moriyama, et al., "Oxidative Dimerization of Methane over Promoted MgO. Important Factors", Chem. Soc. Japan, Chem. Lett., 1165 (1986) (Ba/MgO, Sr/MgO, Ca/MgO); Roos, et al., "The Oxidative Coupling of Methane: Catalyst Requirements and Process Conditions", Studies in Surface Science & Catalysis; #36 Methane Conversion Symp., Auckland, New Zealand, April, 1987, 373, (Ba/MgO); and U.S. Pat. No. 4,780,449 (BaO/La$_2$O$_3$, SrO/La$_2$O$_3$).

European Patent Application Publication No. 206,042 (1986) discloses a number of catalysts for methane coupling including, "a composition consisting essentially of: (1) at least one Group IIA metal, (2) titanium, (3) oxygen and, optionally, (4) at least one material selected from the group consisting of halogen ions . . . said at least one Group IIA metal being present in an amount in excess of any amount present in electrically neutral compounds of said at least one Group IIA metal, said titanium and oxygen" (p. 4)

Matsuhashi, et al., in "Formation of C$_3$ Hydrocarbons from Methane Catalyzed by Na$^+$ Doped ZrO$_2$," Chem Soc. Japan, Chem. Lett., 585 (1989) report that sodium doped zirconia catalysts in oxidative coupling of methane yielded, at 600° C., propane and propene, and state that the C$_2$ hydrocarbons produced were mostly ethane.

Fujimoto, et al., in "Selective Oxidative Coupling of Methane Over Supported Alkaline Earth Metal Halide Catalysts", Appl. Catal., vol. 50, 223 (1989) compare the performance of MgCl$_2$ on MgO, TiO$_2$ and SiO$_2$ supports. The TiO$_2$ and SiO$_2$ catalysts resulted in relatively poor coupling performances.

SUMMARY OF THE INVENTION

By this invention processes are provided for the oxidative coupling of methane to produce heavier hydrocarbon including ethylene and ethane which provide not only good performance, i.e., conversion of alkane and selectivity to higher hydrocarbon, but also are capable of providing desirably high ethylene to ethane mole ratios over extended periods of operation.

In one aspect of this invention catalysts for the oxidative coupling comprise at least one barium or strontium compound (Basic Group IIA Component) having catalytic activity toward the oxidative coupling of methane to produce higher hydrocarbons in intimate association with metal oxide, (metal oxide combustion promoter component) which promotes the oxidation of methane under oxidative coupling conditions to carbon oxides (carbon dioxide and carbon monoxide). Preferably, the metal oxide is selected from Group IVA (especially titanium and zirconium) and Group IIIB (especially aluminum and preferably gallium) metal oxides which promote the formation of carbon oxides. Often, the metal oxide at 700° C. and a space velocity of about 1000 reciprocal hours will convert at least 5, preferably at least 10, say, 10 to 50, per cent of methane in a feed stream of 10 volume percent methane, 5 volume percent oxygen and balance nitrogen ("Oxidation Conditions") to carbon oxides. Hence, low surface area, highly pure alpha-alumina which is relatively inert under Oxidation Conditions, would not be suitable as the metal oxide combustion promoter component.

In another aspect of the invention, catalysts for the oxidative coupling of methane comprise at least one barium or strontium compound having catalytic activity toward the oxidative coupling of methane to produce higher hydrocarbon in intimate association with at least one metal oxide selected from the group consisting of $TiO_2$, $ZrO_2$ and $Ga_2O_3$.

In the oxidative coupling processes of this invention, methane and reactive oxygen-containing material are fed to a reaction zone containing a catalytically effective amount of an oxidative coupling catalyst in the presence of halogen-containing vapor phase additive in an amount sufficient to provide, in combination with the catalyst, an ethylene to ethane ratio of at least about 2.5; the reaction zone is maintained under oxidative coupling conditions to convert at least a portion of the methane to ethylene and ethane and an effluent containing ethylene and ethane produced in the reaction zone is withdrawn.

The catalysts used in this invention appear to be able to provide greater increases in the ethylene to ethane ratio when operated in accordance with the processes of this invention than are provided by similar catalysts, but which do not contain the metal oxide combustion promoter, under similar conditions. Moreover, the processes of this invention are frequently capable of withstanding the presence of higher amounts of halogen component without undue catalyst deactivation, than otherwise similar processes but using a catalyst not containing the metal oxide combustion promoter.

DETAILED DISCUSSION OF THE INVENTION

In accordance with this invention, methane is converted to ethylene and ethane. The methane may be present with other lower alkane, e.g., at least one of ethane and propane. Because of its abundance and the desire to convert it to higher hydrocarbons, methane is the most preferred component in the feed. The products of the conversion are higher hydrocarbons, especially alkanes and alkenes. Because of its widespread use in commodity chemicals, product mixtures exhibiting a high selectivity to ethylene are typically preferred and are provided by the processes of this invention. The reaction is conducted in the presence of a reactive oxygen-containing material (oxidizing material) which for the purposes herein means atomic or molecular oxygen or a compound or chemical complex that contains an oxygen atom available for the oxidative coupling.

The hydrocarbon conversion process is by a cofeed, or simultaneous, process in which both the oxidizing material and the methane-containing feed are provided at the same time to the reaction zone.

In a cofeed mode, the oxidizing material and methane may be introduced by one or more separate streams or, most commonly, in a premixed stream. Generally, the mole ratio of total alkane to active oxygen atom of the oxidizing material (an active oxygen atom is an oxygen atom that is available for oxidation) is at least about 1:2, say, about 1:2 to 50:1, preferably 1:1 to 20:1, The total alkane typically comprises at least about 2 volume percent, e.g., up to about 95, say, 5 to 90, volume percent of the total gases fed to the reaction zone. Frequently, the feed streams are diluted with essentially inert gases such as helium, nitrogen, argon, steam, and carbon dioxide. When diluted, the diluent usually provides between about 5 to 95 volume percent of the feed stream.

The oxidizing material may be any suitable oxygen-bearing material which, under the conditions in the reaction zone, yields an active oxygen atom for the oxidative coupling. While not wishing to be limited to theory, the oxygen atom may be provided as reactive in a gaseous zone and/or may be provided on a catalyst surface as, for instance, reacted, absorbed or adsorbed form. Convenient oxidizing materials are normally gaseous such as molecular oxygen, (e.g., as oxygen, enriched air or air), ozone and gases which yield oxygen such as $N_2O$. Materials that are liquid or solid at ambient conditions may also be used provided that they can be facilely introduced into the reaction zone.

The reaction proceeds at elevated temperatures. Generally, a minimum temperature must be achieved before significant high hydrocarbon production occurs. If the temperature is too high, an undue amount of the hydrocarbon is consumed in oxidation or degradation reactions. Often, the temperature is in the range of about 500° to 1000° C., e.g., about 600° to 800° C. The reactants are usually preheated prior to their introduction into the reaction zone; for instance, to within about 200° C., preferably about 100° C. of the temperature in the reaction zone.

The pressure in the reaction zone may vary widely from less than atmospheric to 100 atmospheres absolute or more often in the range of about 1 to 100, say, 1 to 50, atmospheres absolute.

In general, the reactions proceed rapidly and, hence, the reactants may reside in the reaction zone under reaction conditions for a relatively short period of time, e.g., less than about 30 seconds, often less than about 10 seconds. Frequently, the residence time is about 0.001 to 5, say, 0.1 to 3, seconds. The gas hourly space velocity based on the total gases fed to the reaction zone to the volume of the reaction zone is often about 50 to 50,000, preferably, 500 to 15000, reciprocal hours. Since alkane conversion reactions do not require the presence of a catalyst to proceed, the overall volume of the vessel in which the reaction takes place may be substantially larger than that of the reaction zone containing catalyst. Even so, the volume of the reaction zone is frequently calculated as the volume of the vessel filled with catalyst.

The reaction may be conducted in any suitable reactor capable of providing the reaction temperatures. The reaction may be conducted in a single or in a series of sequential and/or parallel reactors. The catalyst bed may be of any suitable type, including, but not limited to, fixed, fluid, riser, falling, ebulating, and moving bed.

The catalyst size and configuration may vary depending upon the reactor type. For fluid, ebulating and riser reactors, the catalyst is typically between about 30 and 300 microns in major dimension. In fixed bed reactors, the catalyst may be in any suitable configuration including spheres, pellets, cylinders, monoliths, etc., and the size and shape may be influenced by pressure drop considerations for the gases passing through the bed. Often, the catalyst is at least about 0.2 centimeter, say, about 0.5 to 2 centimeters, in major dimension. Monolithic catalysts, which may comprise a support having the catalytically active component thereon or which may be homogeneous, can be sized to fit the reactor volume.

The catalysts of this invention contain a catalytically effective amount of Basic Group IIA Component to effect oxidative coupling. The catalyst also contains a sufficient amount of the metal oxide combustion promoter to enable, in conjunction with the vapor phase halogen component, an ethylene to ethane mole ratio of at least about 2.5:1, preferably at least about 3:1, e.g., about 3:1 to 30:1, and sometimes 5:1 to 20:1, to be obtained. The relative amount of the metal oxide combustion promoter to Basic Group IIA Component should be sufficient that at the vapor phase halogen component feed rates to obtain the desired ethylene to ethane ratio, the performance of the catalyst (i.e., methane conversion and selectivity to ethane and ethylene) are not unduly adversely affected. If too little metal oxide combustion promoter is present, not only may not the high ethylene to ethane ratios be achieved, but also, the catalyst performance may decrease. With too much metal oxide combustion promoter, poor selectivities to ethane and ethylene occur and even with higher vapor phase halogen component levels, satisfactory catayst performance is not achieved.

The amounts of Basic Group IIA Component and metal oxide combustion promoter can, however, vary widely, and will vary depending upon the nature of the components. In general, the weight ratio of Basic Group IIA Component to metal oxide combustion promoter will be between 0.05:10 to 20:1, say, 1:1 to 10.1. In many instances, the metal oxide combustion promoter can readily be obtained in forms suitable as supports and hence, the catalyst may conveniently be a supported catalyst in which the support comprises, in whole or part, the metal oxide combustion promoter. Often, the Basic Group IIA Component is present in an amount of about 0.1 to 30, preferably, about 0.1 to 20, weight percent based on the total weight of the catalyst.

In a preferred aspect of the invention, the amounts of the Basic Group IIA Component and metal oxide combustion promoter are sufficient that under Standard Reference Conditions, as defined below, the yield of $C_2$'s is at least about 15 mole percent based on the methane fed to the reaction zone. In some instances, the yield of $C_2$'s is at least about 20 mole percent under these conditions.

| Standard Reference Conditions | |
|---|---|
| Catalyst | Ground to 30 to 90 mesh (U.S. Sieve Series) |

| -continued | |
|---|---|
| Standard Reference Conditions | |
| Reaction Zone | Approximately 1 to 10 grams. Quartz tube (at catalyst zone) 7 millimeters inside diameter, feed streams mixed immediately before reactor zone. |
| Temperature | 750° C. |
| Pressure | 11 pounds per square inch gauge (176 kpa absolute) |
| GHSV | 800–1200 hr$^{-1}$ |
| Feed | |
| Methane | 10 mole percent |
| Oxygen | 5 mole percent |
| Nitrogen | balance |
| Ethyl chloride | to maximize yield (steady state) |
| Time of determination | When stabilized between 50 and 100 hours of operation. |

The Basic Group IIA Component and metal oxide combustion promoter are in intimate association. While not wishing to be limited to theory, it is believed that the Basic Group IIA Component must sufficiently contact the metal oxide combustion promoter that the combustion activity of the metal oxide combustion promoter is sufficiently attenuated that desirable selectivities to oxidative coupling can occur. Due to the wide variety of suitable Basic Group IIA Components and metal oxide combustion promoters that can be employed, it is not believed necessary that definite chemical compounds need be formed between the components. The Basic Group IIA Component may be deactivating or attenuating the activity of catalytic sites on the metal oxide combustion promoter.

The exact species of the Basic Group IIA Component which is catalytically effective and the precise mechanism by which the catalyst performs the catalytic function is not known. However, a wide variety of barium and strontium compounds appear to be operable. Exemplary of Basic Group IIA Compounds are barium oxide, strontium oxide, barium peroxide, strontium peroxide, barium superoxide, strontium superoxide, barium hydroxide, strontium hydroxide, barium carbonate, strontium carbonate, barium halide ($BaX_2$), strontium halide, barium oxyhalide ($Ba(OX)_2$), strontium oxyhalide, barium halite ($Ba(XO_2)_2$), strontium halite, barium halate ($Ba(XO_3)_2$), strontium halate, barium perhalate ($Ba(XO_4)_2$), strontium perhalate, wherein X is one or more of chlorine, bromine and iodine, and mixtures thereof. The preferred barium compounds are barium oxide, barium dihalide, barium carbonate, and barium hydroxide, and the preferred strontium compounds are strontium oxide, strontium dihalide, strontium carbonate and strontium hydroxide. While other alkaline earth metals have heretofore been proposed for oxidative coupling catalysts such as magnesium oxides and salts and calcium oxides and salts, they appear not to provide either the performances or lifetimes achievable by the catalysts containing barium or strontium compounds.

Metal oxide combustion promoters include oxides and compounds which can convert to oxides under oxidative coupling conditions. Exemplary metal oxides are silica, titanium dioxide, zirconium dioxide, hafnium dioxide, aluminum oxide, (especially with surface areas greater than about 0.2, especially greater than about 0.3, square meter per gram) aluminosilicates (including molecular sieves), and gallium oxide. With many of these metal oxides, forms may exist which do not possess the desired combustion activity. Frequently, the metal oxide combustion promoters have higher surface areas, e.g., at least about 0.5 or more, say 0.5 to 100 or more, square meters per gram, as determined by nitrogen (below 50 m$^2$/g) and krypton (above 50 m$^2$/g) by the B.E.T. method, J. Am. Chem., Soc., vol. 60, 309 (1938). The metal oxide component provided on the catalyst may experience change in form (and surface area) during the oxidative coupling process. For instance, rutile titanium dioxide may be formed from anatase titanium dioxide. Metal oxides such as gamma alumina because of their strong combustion-promoting properties, are sometimes less preferable than other forms of alumina. Group IA and Group IIA metal oxides are not considered herein to be metal oxide combustion promoters. The metal oxide combustion promoter preferably has an acidity of at least about 0.5, say, at least about 0.6, e.g., 0.7 to 5, and sometimes 0.7 to 2, micromoles of acid sites per square meter of surface area. The surface acidity is determined by irreversible ammonia chemisorption at 100° C. of a sample that has been pretreated at 200° C. in helium. When the metal oxide combustion promoter comprises an alpha-aluminum oxide, it preferably has an acidity of at least about 1.25 e.g., at least about 1.5, micromoles of acid sites per square meter of surface area.

The Basic Group IIA Component containing catalysts are preferably supported. The support may comprise the metal oxide combustion promoter, especially titanium dioxide/or zirconium dioxide and/or gallium oxide. The support may be homogeneous or heterogeneous, i.e., with the metal oxide combustion promoter forming only an outer coating, and the supports may contain other than metal oxides, e.g., metal carbonates or other salts, alumina, alkaline earth oxides or carbonates, and Group IIIA metal (including lanthanide series) oxides or carbonates. Often, when used in the support, the metal oxide combustion promoter comprises at least about 20 weight percent, say, 50 to essentially 100, most frequently, 70 to essentially 100, weight percent of the support.

The support is preferably porous and has a surface area (as determined by nitrogen by the B.E.T. method, J. Am. Chem. Soc., vol 60, 309 (1938)) of at least about 0.1, preferably at least about 0.2, say, 0.2 to 60 or 100 or more, square meters per gram.

The catalysts may contain one or more alkali and other alkaline earth metal components. If present, these components are generally in an mole ratio to Basic Group IIA Component of at least 0.01:1, say, about 0.1:1 to 10:1, and typically, 0.1:1 to 1:1. These components comprise the oxides and/or salts of one or more of sodium, lithium, potassium, rubidium, cesium, beryllium, magnesium, and calcium. These compounds may be in the same form as the Basic Group IIA Component, e.g., oxides, hydroxides or salts, or different. Silver and/or silver compound may also be present in an amount sufficient to enhance catalyst performance, e.g., 0.01 to 30, weight percent based on the total weight of the catalyst.

The catalysts used in the processes of this invention may contain other adjuvants such as Group IIIA (including lanthanide series) components such as lanthanum oxide, Group VA components, Group VIA components and manganese. These other adjuvants may be present in amount of about 0.0001 to 10 or more weight percent based on the total weight of the catalyst.

The catalysts may comprise at least one of cobalt, nickel, and rhodium in an amount up to about 2 weight percent based on the weight of the catalyst which amount is sufficient to provide enhanced oxidative coupling activity. Even though a relatively small amount of cobalt, nickel and/or rhodium are present in the catalyst, the processes are able to achieve substantially enhanced alkane conversion at lower bulk reaction temperatures. Moreover, in preferred aspects of the invention, the cobalt and/or nickel and/or rhodium is provided in an amount sufficient to enhance the ethylene to ethane mole ratio in the reactor zone effluent as compared to a similar catalyst which does not contain the aforementioned component under the same conditions. The total amount of cobalt and/or nickel and/or rhodium compound is frequently at least about 0.01, e.g., about 0.01 to 1, say, about 0.2 to 0.8, weight percent (calculated as the metal) based on the total weight of the catalyst. The cobalt, nickel or rhodium may be initially provided on the catalyst in elemental or combined form (e.g., as a nitrate, oxide, hydroxide, carbonate, chloride, etc.). While not wishing to be limited to theory, it is believed that the metal should be maintained in at least a partially chemically combined form (e.g., as in one or more of oxide, carbonate, hydroxide, and halide, especially a chloride, bromide or iodide) during the process. See U.S. patent application Ser. No. 409,375, filed on even date herewith, hereby incorporated by reference.

Supported catalysts may be prepared by any convenient technique. Techniques which have been proposed include coating the catalyst support with a slurry or paste of the ingredients or impregnating the support using a solution or suspension or complex of the ingredients (the impregnation may be simultaneous for all components or sequential). The impregnation may be by an incipient wetness technique or by immersion in the mother liquor or by evaporation of solvent from a solution or suspension containing the support. The catalysts may be dried and, optionally, calcined.

The vapor phase halogen component is provided to the reaction zone during the process. It may be added intermittently or continuously. The halogen component may be provided as a solid, liquid or vapor when added. The halogen component may be halogen, e.g., chlorine, bromium or iodine, or a halogen-containing compound. The halogen-containing compounds (chlorine, bromine and iodine-containing compound) may be inorganic or organic such as hydrogen halide, carbon tetrahalide, methylene halide, methyl dihalide, methyl trihalide, ethyl halide, ethyl dihalide, ethyl trihalide, ethyl tetrahalide, vinyl halide, sulfonyl chloride, phosphonyl chloride, etc. Often, the organic halides have from 1 to 3 halogen atoms and 1 to 3 carbon atoms. The amount of halogen component which can be added to the process, can vary; however, the amount added should be sufficient to provide the desired yield of higher hydrocarbon and the sought ethylene to ethane mole ratio. With either too little or too much halogen component addition, the catalyst performance will be adversely effected. Most frequently, if too little or too much halogen component has been added, good performance can be achieved by altering the rate of halogen component addition.

It has been found that when catalysts containing halide salts are first operated, evolution of a halogen-containing component occurs. This is usually accompanied by high ethylene to ethane ratios being obtained, but these ratios, even in processes according to this invention, tend to decrease. By the processes of this invention, the decreases in the ethylene to ethane ratio can be minimized.

The amount of halogen component to be added for a given catalyst system will depend inter alia, on the Basic Group IIA Component and the metal oxide combustion promoter. Moreover, the optimum amount may change with the use of the catalyst.

Also, the type of halogen being added will influence the performance of the reaction system. In general, a process using a bromine compound as the halogen will provide a higher ratio of ethylene to ethane than a similar process using chlorine compound as the halogen. Within these guidelines, the amount of continuous vapor phase addition of the halogen component is often within the range of 5 to 5000, say, 10 to 1000, parts per million by volume based on the volume of feed to the reaction zone.

A volatilized metal component may be introduced intermittently or continuously into the reaction zone in an amount sufficient to reduce the rate of vapor phase alkane conversion reaction. Enhancements in selectivities to higher hydrocarbons may be obtained using the volatilized metal component additive, and the selectivity benefits provided by the catalysts better realized. See U.S. patent application Ser. No. 409,361, filed on even date herewith, hereby incorporated by reference.

In practice, the amount of volatilized metal component to be added can be ascertained by monitoring the selectivity to higher hydrocarbons and adjusting the amount introduced. The amount of volatilized metal component introduced can vary widely and will depend, to some extent, on the nature of the volatilized metal component. Often, the amount of volatilized metal component introduced is at least about 0.001 picogram, say, about 0.005 picogram to 10,000 or more milligrams per cubic meter of alkane in the feed (determined at standard temperature and pressure ("STP")).

It is not essential, and indeed in most instances it is not the case, that the volatilized metal component has a boiling point below the reaction temperature. Most convenient volatilized metal components have boiling points much higher than the reaction temperature under reaction conditions. However, the volatilized metal component should have a vapor pressure under the reaction conditions sufficient to provide the sought amount of volatilized metal component to achieve the sought reduction in vapor phase alkane conversion. Accordingly, the volatilized metal components are preferably molten or near to becoming molten (e.g., within 100° C.) at the reaction temperature. The melting points of some volatilized metal components are set forth in Table I.

TABLE I

| VOLATILIZED COMPONENT | APPROXIMATE MELTING POINT (°C.) |
|---|---|
| Barium chloride | 963 |
| Strontium chloride | 875 |
| Barium bromide | 847 |
| Sodium chloride | 801 |
| Calcium chloride | 782 |
| Potassium chloride | 770 |
| Sodium bromide | 758 |
| Barium iodide | 740 |
| Potassium bromide | 730 |
| Rubidium chloride | 718 |
| Potassium iodide | 686 |
| Sodium iodide | 653 |
| Cesium chloride | 645 |

TABLE I-continued

| VOLATILIZED COMPONENT | APPROXIMATE MELTING POINT (°C.) |
|---|---|
| Strontium bromide | 643 |
| Cesium iodide | 612 |
| Lithium chloride | 605 |
| Barium hydroxide | 408 |
| Potassium hydroxide | 405 |
| Sodium hydroxide | 318 |
| Cesium hydroxide | 272 |

The preferred volatilized metal components are salts of Group IA and Group IIA metals. Salts such as nitrates, chromates, etc., may have explosive characteristics at the reaction temperatures. Thus, these salts and others which may adversely decompose or oxidize are generally avoided. The volatilized metal component, however, may be added in the form of an oxide, hydroxide, peroxide, superoxide or salt and be converted to another compound under the reaction conditions. In general, the preferred salts are halides, especially chlorides, bromides and iodides.

The introduction of the volatilized metal component into the reaction zone may be by any convenient means. Advantageously, the volatilized metal component is relatively uniformly distributed as it passes through the reaction zone. The introduction may be, for instance, by adding a stream of volatilized metal component in the vapor form to the reaction zone or to the feed stream. Since most volatilized metal components are not gases under the reaction conditions, the volatilized metal components must enter the vapor phase through sublimation or the effects of partial pressure over the metal component in the liquid state. Hence, it is often desirable to pass, at an elevated temperature (e.g. 400° to 1000° C., say, 500° to 850° C.), all or a portion of the feed gas over the metal component to volatilize a desired amount of the metal component. Since oxidation reactions can occur at these elevated temperatures, frequently the volatilized metal component is contacted with either an alkane-containing stream having an essential absence of oxygen or a diluent gas or an oxygen-containing stream having an essential absence of alkane. The stream can be admixed with the remaining portion of the feed gases (for a continuous process).

In the event that the volatilized metal component solidifies, coalesces or is adsorbed or absorbed in the reaction zone, a build-up of the volatilized metal component may occur. In many instances, the build-up is not unduly deleterious; however, if it adversely affects the performance of the reaction, temporary cessation of the introduction of the volatilized metal component may be indicated.

The following examples are provided by way of illustration of the invention and are not in limitation thereof. All parts and percentages of solids are by weight and of liquids and gases are by volume unless otherwise noted or clear from the context.

Catalysts are made by one of two general procedures, Procedure A or Procedure B. The proper mesh of support is obtained from sieving and/or grinding and sieving supports prior to Procedures A and B. In Procedure A, supported catalysts are prepared using the incipient wetness technique. In this procedure, the amounts of components required to give the desired loadings are dissolved in a quantity of deionized, distilled water necessary to just fill the pores of the support. The solution is then added to the support particles. In some cases, if the dopants are not easily soluble, suspensions of the components are added to the support. The resulting material is dried in a vacuum oven at 130° C. under a vacuum of 16-84 kPa for 1 to 50 hours (preferred 16-20 hours). Some of the dried catalysts are either tested without further treatment or first calcined in air at atmospheric pressure (usually at 800° C. to 850° C.). Metal or inorganic compound loadings are expressed as weight percent based on 100 weight percent catalyst.

In Procedure B, supported catalysts are prepared by adding the proper amount of component(s) to a mixture of water which is stirred with the support, while heating in a glass container on a hotplate for 2 to 3 hours (or until almost no water is left), to distribute the material in and on the support. If the dopants are not easily soluble, they are finely ground first. Deionized, distilled water is used (50 milliliters unless stated otherwise). The resulting material is dried in a vacuum oven at 130° C. under a vacuum of 16-84 kPa for 1 to 50 hours (preferred 16-20 hours). Some of the dried catalysts are then calcined in air at atmospheric pressure (usually at 850° C.). Metal or inorganic compound loadings are expressed as weight percent based on 100 weight percent catalyst.

The catalysts are evaluated using a reactor system containing two parallel reactors to which may be fed a variety of gases. The reactor system consists of a gas feed system, two tubular microreactors (a steam feed system to one of these), two Lindberg tube furnaces, two liquid collection systems, an on-line gas analyzer with a stream selector, and a separate liquids analyzer.

Two Lindberg Mini-Mite (TM), model 55035, tube furnaces (800 watts, 115 volts, 1100° C. maximum operating temperature) are used for heating the tubular microreactors. The entire cylindrical heated chamber is comprised of two halves, making up the split-hinge furnace design. Each half is a composite unit of Moldatherm (TM), Lindberg's high temperature ceramic fiber insulation, and a helically coiled alloy heating element.

Quartz reactors are used. These include Reactor A, Reactor C, and Reactor D. Reactors are operated vertically.

Reactor A is constructed of 1.5 centimeters inside diameter quartz tubing (1.7 cm o. d.) with thermocouple wells of 0.3 centimeter i. d quartz tubing (0.5 cm o. d.) positioned along the center of the reactors. The thermocouple well in Reactor A extends through the catalyst bed (into the preheater region) which allows the temperatures of the preheater, catalyst bed and post-catalyst region to be monitored. Reactor A is 56.5 centimeters long, and the thermocouple well extends 33.75 centimeters into the reactor. The bottom of the heated region of the reactor is 12.75 centimeters above the bottom of the reactor. The top of the heated region is 46.75 centimeters above the bottom of the reactor. The post-catalyst volume is packed with 20/40 or 14/30 mesh (U.S. Sieve Series) quartz chips in order to minimize the high temperature post-catalyst residence time of the products, and to hold the catalyst in place. The bottom end of the reactor is connected to 1.0 centimeters inside diameter (1.2 centimeters o. d.) quartz tubing at a right angle to the reactor.

The center of the catalyst bed is 18.5 centimeters above the bottom of the oven, or 31.25 centimeters above the bottom of the reactor. When the center of the reactor is heated to 802° C. under typical flow rates of gases, the bottom of the heated portion of the reactor is about 645° C.

Reactor C is constructed of 0.9 centimeters inside diameter quartz tubing (1.1 centimeters o. d.). Reactor C is 56.5 centimeters long. The bottom of the heated region of the reactor is 12.75 centimeters above the bottom of the reactor. The top of the heated region is 46.75 centimeters above the bottom of the reactor. The post-catalyst volume is packed with 20/40 or 14/30 mesh (U.S. Sieve Series) quartz chips in order to minimize the high temperature post-catalyst residence time of the products, and to hold the catalyst in place. The bottom end of the reactor is connected to 1.0 centimeter inside diameter (1.2 centimeters o. d.) quartz tubing at a right angle to the reactor. The ends of the reactor are made of quartz "O"-ring joints (1.5 centimeters i. d. at the inlet and 0.9 cm i. d. at the outlet) which allow easy placement of the reactor into the system.

The center of the catalyst bed is 18.5 centimeters above the bottom of the oven, or 31.25 centimeters above the bottom of the reactor. A similar temperature profile as in Reactor A is exhibited by Reactor C.

The top 30.5 centimeters of reactor D is constructed of 0.9 centimeters inside diameter quartz tubing (1.1 cm o. d.). This is connected to 26 centimeters of 3 millimeters inside diameter (5 mm o. d.) quartz tubing. Reactor C is 56.5 centimeters long. The bottom of the heated region of the reactor is 12.75 centimeters above the bottom of the reactor. The top of the heated region is 43.75 centimeters above the bottom of the reactor. The post-catalyst volume of the wider part of the reactor is packed with 20/40 or 14/30 mesh quartz chips, quartz wool, or both quartz chips and quartz wool in order to minimize the high temperature post-catalyst residence time of the products, and to hold the catalyst in place. The bottom end of the reactor is connected to 1.0 centimeter inside diameter (1.2 cm o. d.) quartz tubing at a right angle to the reactor.

The center of the catalyst bed is 18.5 centimeters above the bottom of the oven, or 31.25 centimeters above the bottom of the reactor. Reactor D exhibits a similar temperature profile to that of Reactor A.

The catalyst bed is formed in Reactor D by providing quartz chips within the range of 14 to 40 mesh (U.S. Sieve Series) below and above the catalyst bed, which is separated from the quartz ships by quartz wool. The length of the catalyst bed along the reactor varies, depending on the weight of catalyst used, the density of the catalyst, and the type of reactor used. Most catalysts are within the range of 30 to 100 mesh (U. S. Sieve Series), with many from 30 to 60 mesh and many from 60 to 100 mesh.

In the general operating procedure, the reactors are filled with washed quartz chips above and below the catalyst bed. Those portions of Reactor D with tubing of 0.3 centimeter i. d. are not filled with quartz. Quartz wool is used to separate quartz chips from the catalyst bed and to hold quartz chips in the reactor. Undiluted catalysts of varying mesh sizes are used except in cases where the catalyst is only available as a fine powder. In these cases, it is diluted with quartz chips within the 14 to 40 mesh range.

Charged reactors are pressurized under nitrogen to about 176 kPa absolute (11 pounds per square inch guage), then flushed with nitrogen during heating. Gas mixtures entering and exiting the reactor system during reactions are analyzed at intervals using gas chromatography. The reactor pressure is maintained at about 176 kPa throughout the reaction, and nitrogen is the diluent gas. The feed for most experiments contains $CH_4/O_2/N_2$ in a mole ratio of about 2/1/17. After experiments, the reactant flow is terminated and the reactor is flushed with nitrogen while cooling. In the tables, the following defined terms are used.

| | |
|---|---|
| Temperature (Temp) | Temperature of the catalyst bed (C.). |
| Time | Time since reactant flow is started (minutes). |
| $CH_4C$ | Mole % of methane reacted. |
| Sel | Selectivity to ethane + ethylene expressed as a percent, based on methane reacted. |
| Yield | Mole % of methane converted to $C_2$'s, calculated as ($CH_4$ conversion) × ($C_2$ selectivity)/100. |
| =/— | Mole ratio of ethylene to ethane in the product stream. |
| $CO_2/CO$ | Mole ratio of carbon dioxide to carbon monoxide in the product stream. |
| GHSV | Gas hourly space velocity (reciprocal hours) (STP). |
| $CH_4$ In | Mole % of methane introduced in the feed stream. |
| $O_2$ In | Mole % of oxygen introduced in the feed stream. |
| ECl | Ethyl chloride feed rate in parts per million by volume based on total feed. |
| EBr | Ethyl bromide feed rate in parts per million by volume based on total feed. |

EXAMPLE 1

A 5 weight percent barium carbonate (3.5 weight percent barium) on titanium dioxide catalyst is prepared by the general procedure B set forth above using 0.3 gram of barium carbonate (from Johnson Matthey/AESAR Group, Seabrook, N.H., Lot number S96252B, 99.997 weight percent) and 6.0 grams of titanium dioxide (from Johnson Matthey/AESAR Group, Seabrook, N.H., Lot number S96579, 99.995 weight percent) except 40 milliliters of water are used. The catalyst is calcined at 850° C. for 4 hours. The catalyst particle size is 60 to 100 mesh (U.S. Sieve Series). The performance of the catalyst using the equipment and procedures described above is presented in Table II. Reactor D is used with 5.0 grams of catalyst. As can be seen, the amount of halogen component has a demonstrable effect on the performance of the catalyst.

TABLE II

| Temp °C. | $CH_4C$ % | Sel % | Yield % | =/— | $CO_2/CO$ | $CH_4$ in Mole % | $O_2$ in Mole % | Time Min. | GHSV hr−1 | ECl ppmv |
|---|---|---|---|---|---|---|---|---|---|---|
| 750 | 22.0 | 8.5 | 1.9 | 0.7 | 0.9 | 10.4 | 5.1 | 30 | 2743 | 6 |
| 750 | 21.0 | 9.2 | 1.9 | 0.8 | 0.8 | 10.4 | 5.1 | 120 | 2743 | 6 |
| 750 | 17.4 | 13.2 | 2.3 | 0.7 | 0.7 | 10.2 | 4.9 | 4845 | 2743 | 6 |
| 750 | 15.9 | 14.1 | 2.2 | 0.7 | 0.7 | 10.0 | 5.2 | 7050 | 2743 | 6 |
| 750 | 30.3 | 40.6 | 12.4 | 4.9 | 0.3 | 10.2 | 5.2 | 8850 | 2743 | 500 |
| 750 | 31.1 | 49.2 | 15.3 | 5.4 | 0.3 | 10.2 | 5.2 | 8985 | 2743 | 500 |
| 750 | 30.9 | 59.4 | 18.1 | 5.6 | 0.3 | 10.3 | 5.0 | 9570 | 2743 | 500 |
| 750 | 31.4 | 59.2 | 18.4 | 5.9 | 0.3 | 10.2 | 5.2 | 9630 | 2743 | 500 |
| 750 | 30.9 | 60.1 | 18.4 | 5.8 | 0.3 | 10.2 | 5.2 | 9720 | 2743 | 500 |
| 750 | 31.1 | 63.2 | 19.1 | 5.6 | 0.3 | 10.2 | 4.9 | 11430 | 2743 | 500 |
| 750 | 38.8 | 54.5 | 20.5 | 8.4 | 0.3 | 10.2 | 4.9 | 11520 | 1714 | 500 |
| 750 | 38.9 | 53.9 | 20.4 | 8.5 | 0.3 | 10.2 | 4.9 | 11610 | 1714 | 500 |
| 750 | 37.9 | 53.7 | 20.1 | 8.4 | 0.3 | 10.2 | 5.1 | 12915 | 1714 | 500 |
| 750 | 34.3 | 54.6 | 18.5 | 5.9 | 0.5 | 10.2 | 4.9 | 13005 | 1714 | 250 |
| 750 | 34.3 | 53.9 | 18.2 | 5.8 | 0.5 | 10.2 | 4.9 | 13095 | 1714 | 250 |
| 750 | 33.4 | 53.3 | 17.7 | 5.7 | 0.5 | 10.3 | 5.3 | 13815 | 1714 | 250 |
| 750 | 33.9 | 52.6 | 17.7 | 5.8 | 0.5 | 10.3 | 5.2 | 13950 | 1714 | 250 |
| 750 | 34.3 | 52.3 | 17.7 | 5.8 | 0.5 | 10.3 | 5.2 | 14040 | 1714 | 250 |
| 750 | 34.9 | 52.0 | 17.8 | 5.8 | 0.5 | 10.3 | 5.2 | 14220 | 1714 | 250 |
| 750 | 34.9 | 52.0 | 17.8 | 5.8 | 0.5 | 10.3 | 5.2 | 14310 | 1714 | 250 |
| 750 | 30.9 | 61.6 | 18.7 | 5.7 | 0.3 | 10.2 | 5.1 | 14385 | 2743 | 500 |
| 750 | 30.5 | 61.9 | 18.6 | 5.6 | 0.3 | 10.2 | 5.1 | 14460 | 2743 | 500 |
| 750 | 23.9 | 65.5 | 15.5 | 4.0 | 0.3 | 16.1 | 5.4 | 14535 | 2743 | 500 |
| 750 | 23.9 | 65.5 | 15.5 | 4.0 | 0.3 | 16.1 | 5.4 | 14625 | 2743 | 500 |
| 750 | 24.8 | 66.0 | 16.0 | 3.9 | 0.3 | 16.0 | 5.1 | 16020 | 2743 | 500 |
| 750 | 23.3 | 65.9 | 15.3 | 3.9 | 0.3 | 16.3 | 5.2 | 18225 | 2743 | 500 |
| 750 | 30.3 | 58.2 | 17.3 | 5.9 | 0.3 | 16.2 | 5.1 | 18360 | 1714 | 500 |
| 750 | 30.4 | 58.7 | 17.4 | 5.9 | 0.4 | 16.2 | 5.1 | 18450 | 1714 | 500 |
| 750 | 44.9 | 48.8 | 21.8 | 11.3 | 0.3 | 7.3 | 5.1 | 18540 | 1714 | 500 |
| 750 | 44.1 | 49.5 | 21.9 | 11.3 | 0.3 | 7.3 | 5.1 | 18610 | 1714 | 500 |
| 750 | 34.2 | 59.1 | 20.5 | 7.3 | 0.3 | 7.3 | 5.1 | 18690 | 2743 | 500 |
| 750 | 34.6 | 58.2 | 20.5 | 7.4 | 0.3 | 7.3 | 5.1 | 18780 | 2743 | 500 |
| 750 | 37.7 | 58.1 | 21.7 | 8.0 | 0.3 | 6.2 | 5.1 | 18855 | 2743 | 500 |
| 750 | 38.0 | 58.2 | 21.9 | 8.0 | 0.3 | 6.2 | 5.1 | 18945 | 2743 | 500 |
| 750 | 37.2 | 60.8 | 22.2 | 7.5 | 0.3 | 6.4 | 5.1 | 19485 | 2743 | 500 |
| 750 | 36.9 | 60.9 | 22.1 | 7.4 | 0.3 | 6.4 | 5.1 | 19665 | 2743 | 500 |
| 750 | 37.4 | 59.0 | 21.9 | 7.9 | 0.3 | 6.4 | 4.9 | 19800 | 2743 | 500 |
| 750 | 38.2 | 58.5 | 22.0 | 8.1 | 0.3 | 6.4 | 4.9 | 19890 | 2743 | 500 |
| 750 | 38.9 | 58.5 | 22.2 | 8.2 | 0.3 | 6.4 | 4.9 | 19980 | 2743 | 500 |
| 750 | 38.1 | 58.9 | 22.1 | 8.1 | 0.3 | 6.4 | 5.1 | 20070 | 2743 | 500 |
| 770 | 48.0 | 47.8 | 23.1 | 11.1 | 0.3 | 6.4 | 5.1 | 20160 | 2743 | 500 |
| 730 | 30.3 | 63.3 | 18.8 | 5.8 | 0.2 | 6.4 | 5.1 | 20210 | 2743 | 500 |
| 750 | 39.0 | 58.2 | 22.2 | 8.2 | 0.3 | 6.4 | 5.1 | 20295 | 2743 | 500 |
| 750 | 38.6 | 58.7 | 22.2 | 8.1 | 0.3 | 6.4 | 5.1 | 20385 | 2743 | 500 |
| 750 | 38.8 | 58.4 | 22.3 | 8.2 | 0.3 | 6.3 | 4.8 | 20565 | 2743 | 500 |
| 750 | 37.8 | 58.5 | 22.0 | 8.1 | 0.3 | 6.4 | 5.1 | 21105 | 2743 | 500 |
| 750 | 47.1 | 47.4 | 22.6 | 12.8 | 0.3 | 6.2 | 5.0 | 21240 | 1714 | 500 |
| 750 | 47.5 | 47.2 | 22.5 | 12.8 | 0.3 | 6.2 | 5.0 | 21330 | 1714 | 500 |

EXAMPLE 2

A 5 weight percent barium chloride (3.5 weight percent barium) on gallium oxide catalyst is prepared by the general procedure A set forth above using 0.27 gram of barium chloride (from Johnson Matthey/AESAR Group, Seabrook, N.H., Lot number S94730, 99.9999 weight percent) and 5 grams of gallium oxide (from Johnson Matthey/AESAR Group, Seabrook, N.H., Lot number S70392, 99.999 weight percent, B.E.T. surface area 4.22 square meters per gram). The catalyst particle size is 30 to 60 mesh (U.S. Sieve Series). The performance of the catalyst using the equipment and procedures described above is presented in Table II. Reactor D is used with 5.0 grams of catalyst.

equipment and procedures described above is presented in Table IV. Reactor D is used with 5.0 grams of catalyst. As can be seen, the ethylene to ethane ratio rapidly decreases after initial operation of the barium chloride catalyst, but the ratio is regained upon commencing the flow of ethyl chloride.

TABLE IV

| Temp °C. | CH$_4$C % | Sel % | Yield % | =/− | CO$_2$/CO | CH$_4$ in Mole % | O$_2$ in Mole % | Time Min. | GHSV hr−1 | ECl ppmv |
|---|---|---|---|---|---|---|---|---|---|---|
| 750 | 38.2 | 47.9 | 18.1 | 11.0 | 0.4 | 9.8 | 5.2 | 30 | 878 | 0 |
| 750 | 38.1 | 46.2 | 17.4 | 10.6 | 0.4 | 9.8 | 5.2 | 140 | 878 | 0 |
| 750 | 37.0 | 44.9 | 16.5 | 9.7 | 0.5 | 9.8 | 5.2 | 230 | 878 | 0 |
| 750 | 36.4 | 42.8 | 15.5 | 8.8 | 0.6 | 9.8 | 5.2 | 320 | 878 | 0 |
| 750 | 35.5 | 41.0 | 14.5 | 8.0 | 0.7 | 9.8 | 5.2 | 410 | 878 | 0 |
| 750 | 36.0 | 38.4 | 13.6 | 6.5 | 0.8 | 9.8 | 4.7 | 590 | 878 | 0 |
| 750 | 36.7 | 35.9 | 12.7 | 5.5 | 0.9 | 9.8 | 4.7 | 770 | 878 | 0 |
| 750 | 34.8 | 32.8 | 11.3 | 4.9 | 1.0 | 9.8 | 4.7 | 950 | 878 | 0 |
| 750 | 33.2 | 31.3 | 10.4 | 4.5 | 1.1 | 9.7 | 4.6 | 1085 | 878 | 0 |
| 750 | 33.7 | 30.2 | 10.1 | 4.4 | 1.1 | 9.7 | 4.6 | 1175 | 878 | 0 |
| 750 | 33.1 | 29.5 | 9.8 | 4.2 | 1.1 | 9.7 | 4.6 | 1265 | 878 | 0 |
| 750 | 33.2 | 28.7 | 9.5 | 4.0 | 1.2 | 9.7 | 4.6 | 1355 | 878 | 0 |
| 750 | 33.0 | 28.2 | 9.3 | 3.9 | 1.2 | 9.7 | 4.6 | 1400 | 878 | 0 |
| 750 | 39.1 | 41.7 | 16.3 | 10.3 | 0.5 | 10.1 | 4.6 | 1535 | 878 | 500 |
| 750 | 39.0 | 42.2 | 16.5 | 10.5 | 0.5 | 10.1 | 4.6 | 1670 | 878 | 500 |
| 750 | 39.0 | 42.4 | 16.6 | 10.5 | 0.5 | 10.1 | 4.6 | 1850 | 878 | 500 |
| 750 | 39.7 | 42.5 | 16.8 | 10.5 | 0.5 | 10.4 | 4.9 | 2030 | 878 | 500 |
| 750 | 39.2 | 42.3 | 16.6 | 10.5 | 0.5 | 10.4 | 4.9 | 2210 | 878 | 500 |
| 750 | 38.9 | 42.5 | 16.6 | 10.5 | 0.5 | 10.4 | 4.9 | 2390 | 878 | 500 |
| 750 | 38.4 | 42.7 | 16.5 | 10.4 | 0.5 | 10.1 | 5.1 | 2525 | 878 | 500 |

TABLE III

| Temp °C. | CH$_4$C % | Sel % | Yield % | =/− | CO$_2$/CO | CH$_4$ in Mole % | O$_2$ in Mole % | Time Min. | GHSV hr−1 | ECl ppmv |
|---|---|---|---|---|---|---|---|---|---|---|
| 750 | 40.2 | 46.5 | 18.5 | 11.5 | 58.9 | 9.9 | 5.1 | 70 | 900 | 50 |
| 750 | 41.7 | 48.4 | 19.9 | 8.5 | 216.8 | 9.9 | 5.1 | 145 | 900 | 50 |
| 750 | 42.6 | 49.0 | 20.5 | 7.3 | 183.5 | 9.9 | 5.1 | 275 | 900 | 50 |
| 750 | 38.5 | 44.8 | 17.4 | 4.9 | 42.6 | 10.0 | 5.1 | 995 | 900 | 50 |
| 750 | 40.9 | 48.5 | 19.5 | 4.5 | 9.3 | 10.1 | 5.3 | 1125 | 1500 | 50 |
| 800 | 37.1 | 39.2 | 14.4 | 4.2 | 46.7 | 10.1 | 5.3 | 1205 | 2100 | 50 |

EXAMPLE 3

A 5 weight percent barium chloride (3.5 weight percent barium) on titanium dioxide catalyst is prepared by the general procedure A set forth above using 0.27 gram of barium chloride (from Johnson Matthey/AESAR Group, Seabrook, N.H., Lot number S94730, 99.9999 weight percent) and 5.00 grams of titanium dioxide (from Johnson Matthey/AESAR Group, Seabrook, N.H., Lot number S96579, 99.995 weight percent, B.E.T. surface area 0.82 square meter per gram). The catalyst particle size is 30 to 60 mesh (U.S. Sieve Series). The performance of the catalyst using the

EXAMPLE 4

A 5 weight percent barium carbonate (3.5 weight percent barium) on zirconium dioxide catalyst is prepared by the general procedure B set forth above using 0.301 gram of barium carbonate (from Johnson Matthey/AESAR Group, Seabrook, N.H., Lot number S96252B, 99.997 weight percent) and 6.0 grams of zirconium dioxide (from Johnson Matthey/AESAR Group, Seabrook, N.H., Lot number S96307, 99.9975 weight percent, B.E.T. surface area 0.95 square meter per gram). The catalyst is calcined at 850° C. for 2 hours. The catalyst particle size is 60 to 100 mesh (U.S. Sieve Series). Reactor D is used with 5.0 grams of catalyst diluted with 2 cubic centimeters of quartz chips of particle size of 14 to 30 mesh (U.S. Sieve Series). The results of evaluating the catalyst using the equipment and procedures described above are set forth in Table V. A high space velocity (5053 hr-1) is used. A higher ethylene to ethane ratio is achieved when ethyl chloride level is raised from 10 to 200 ppmv.

TABLE V

| Temp °C. | CH$_4$C % | Sel % | Yield % | =/− | CO$_2$/CO | CH$_4$ in Mole % | O$_2$ in Mole % | Time Min. | GHSV hr−1 | ECl ppmv |
|---|---|---|---|---|---|---|---|---|---|---|
| 750 | 37.1 | 24.7 | 9.1 | 1.3 | 5.4 | 9.3 | 4.6 | 45 | 5053 | 10 |
| 750 | 36.9 | 26.1 | 9.6 | 1.3 | 4.8 | 9.3 | 4.6 | 185 | 5053 | 10 |
| 750 | 37.3 | 27.4 | 10.1 | 1.4 | 4.5 | 9.5 | 4.8 | 365 | 5053 | 10 |
| 750 | 37.2 | 28.8 | 10.6 | 1.4 | 4.4 | 9.6 | 4.8 | 590 | 5053 | 10 |
| 750 | 37.3 | 29.7 | 10.9 | 1.4 | 4.4 | 9.6 | 4.8 | 770 | 5053 | 10 |
| 750 | 37.2 | 30.2 | 11.1 | 1.4 | 4.3 | 9.6 | 4.8 | 950 | 5053 | 10 |

TABLE V-continued

| Temp °C. | CH4C % | Sel % | Yield % | =/− | CO2/CO | CH4 in Mole % | O2 in Mole % | Time Min. | GHSV hr−1 | ECl ppmv |
|---|---|---|---|---|---|---|---|---|---|---|
| 750 | 37.0 | 30.2 | 11.1 | 1.4 | 4.2 | 9.6 | 4.8 | 1085 | 5053 | 10 |
| 750 | 37.1 | 30.6 | 11.2 | 1.4 | 4.1 | 9.6 | 4.8 | 1445 | 5053 | 10 |
| 750 | 36.2 | 30.6 | 11.0 | 1.4 | 3.9 | 9.7 | 4.8 | 1805 | 5053 | 10 |
| 750 | 36.0 | 30.0 | 10.7 | 1.4 | 3.7 | 9.7 | 4.7 | 2210 | 5053 | 10 |
| 750 | 35.6 | 29.0 | 10.3 | 1.4 | 3.5 | 9.5 | 4.6 | 2525 | 5053 | 10 |
| 750 | 34.5 | 28.6 | 9.9 | 1.4 | 3.2 | 9.5 | 4.6 | 2885 | 5053 | 10 |
| 750 | 34.9 | 27.8 | 9.6 | 1.4 | 3.0 | 9.7 | 4.7 | 3245 | 5053 | 10 |
| 750 | 34.5 | 26.6 | 9.2 | 1.4 | 2.8 | 9.7 | 5.0 | 3650 | 5053 | 10 |
| 750 | 34.7 | 26.0 | 8.9 | 1.4 | 2.7 | 9.7 | 4.7 | 3965 | 5053 | 10 |
| 750 | 34.7 | 25.2 | 8.6 | 1.4 | 2.6 | 9.7 | 4.7 | 4325 | 5053 | 10 |
| 750 | 34.2 | 24.0 | 8.3 | 1.4 | 2.5 | 9.8 | 4.9 | 4685 | 5053 | 10 |
| 750 | 34.0 | 23.9 | 8.1 | 1.4 | 2.4 | 9.8 | 5.0 | 5090 | 5053 | 10 |
| 750 | 30.3 | 34.7 | 10.5 | 2.2 | 1.1 | 9.6 | 5.1 | 6530 | 5053 | 200 |
| 750 | 29.8 | 36.0 | 10.8 | 2.5 | 0.6 | 9.5 | 5.0 | 6845 | 5053 | 200 |
| 750 | 28.1 | 42.8 | 12.0 | 2.7 | 0.4 | 9.5 | 5.0 | 7205 | 5053 | 200 |
| 750 | 27.7 | 42.9 | 11.9 | 2.8 | 0.3 | 9.5 | 4.8 | 7565 | 5053 | 200 |
| 750 | 27.8 | 42.9 | 11.9 | 2.8 | 0.3 | 9.4 | 4.8 | 7970 | 5053 | 200 |

EXAMPLE 5

A 5 weight percent barium chloride (3.5 weight percent barium) on zirconium dioxide catalyst is prepared by the general procedure A set forth above using 0.6 gram of barium chloride (from Johnson Matthey/AESAR Group, Seabrook, N.H., Lot number S94730, 99.9999 weight percent) and 10.0 grams of zirconium dioxide (from Johnson Matthey/AESAR Group, Seabrook, N.H., Lot number S96307, 99.9975 weight percent, B.E.T. surface area 0.95 square meter per gram). The catalyst particle size is 60 to 100 mesh (U.S. Sieve Series). The catalyst is evaluated for oxidative coupling of methane, using the equipment and procedures described above, and the results are set forth in Table VI. Reactor D is used with 5.0 grams of catalyst. An improvement in ethylene to ethane ratio is obtained by restarting the ethyl chloride.

TABLE VI

| Temp °C. | CH4C % | Sel % | Yield % | =/− | CO2/CO | CH4 in Mole % | O2 in Mole % | Time Min. | GHSV hr−1 | ECl ppmv |
|---|---|---|---|---|---|---|---|---|---|---|
| 750 | 42.6 | 34.0 | 14.2 | 4.3 | 1.7 | 10.3 | 5.3 | 35 | 1200 | 0 |
| 750 | 40.8 | 35.9 | 14.7 | 2.8 | 2.4 | 10.3 | 5.3 | 245 | 2000 | 50 |
| 750 | 39.9 | 35.4 | 14.3 | 2.9 | 2.2 | 10.3 | 5.3 | 425 | 2000 | 50 |
| 750 | 38.5 | 34.8 | 13.8 | 3.0 | 1.8 | 10.3 | 5.1 | 6725 | 2000 | 50 |
| 775 | 41.8 | 40.7 | 17.3 | 3.0 | 2.4 | 10.3 | 5.1 | 6875 | 3200 | 50 |
| 775 | 41.7 | 41.0 | 17.4 | 2.9 | 2.5 | 10.3 | 5.1 | 6915 | 3200 | 50 |
| 800 | 44.0 | 45.1 | 19.9 | 3.4 | 2.6 | 10.3 | 5.1 | 6995 | 3200 | 50 |
| 800 | 44.9 | 44.5 | 20.0 | 3.5 | 2.7 | 10.3 | 5.1 | 7040 | 3200 | 50 |
| 800 | 46.0 | 44.7 | 20.1 | 3.5 | 2.8 | 10.3 | 5.1 | 7085 | 3200 | 0 |
| 800 | 46.6 | 44.1 | 20.0 | 3.5 | 2.7 | 10.3 | 5.1 | 7130 | 3200 | 0 |
| 800 | 43.5 | 41.9 | 18.3 | 3.1 | 3.3 | 9.9 | 5.1 | 7310 | 3200 | 0 |
| 800 | 37.1 | 32.0 | 12.0 | 1.7 | 5.3 | 9.9 | 5.2 | 7670 | 3200 | 0 |
| 800 | 37.6 | 30.5 | 11.5 | 1.7 | 5.0 | 9.9 | 4.8 | 8255 | 3200 | 0 |
| 800 | 41.3 | 35.4 | 14.7 | 2.7 | 2.7 | 10.2 | 5.1 | 8435 | 3200 | 50 |
| 800 | 40.8 | 35.4 | 14.5 | 2.7 | 2.5 | 10.2 | 5.1 | 8525 | 3200 | 50 |
| 800 | 38.3 | 34.2 | 13.4 | 2.7 | 2.4 | 10.2 | 5.2 | 9470 | 3200 | 50 |

EXAMPLE 6

(Comparative)

Barium chloride (from Johnson Matthey/AESAR Group, Seabrook, N.H., Lot number S94730, 99.9999 weight percent, 100 to 140 mesh, U.S. Sieve Series) is evaluated as a catalyst after heating in air for 18 hours at 130° C. and atmospheric pressure. Reactor D is used with 1.0 gram of catalyst. The results are provided in Table VII. The catalyst is relatively poor. Even with the addition of ethyl chloride low ethylene to ethane ratios are obtained.

TABLE VII

| Temp °C. | CH4C % | Sel % | Yield % | =/− | CO2/CO | CH4 in Mole % | O2 in Mole % | Time Min. | GHSV hr−1 | ECl ppmv |
|---|---|---|---|---|---|---|---|---|---|---|
| 750 | 1.7 | 49.3 | 0.8 | 0.2 | 0.4 | 9.8 | 5.3 | 95 | 5143 | 0 |
| 750 | 1.5 | 49.0 | 0.8 | 0.2 | 0.4 | 9.8 | 5.3 | 230 | 5143 | 0 |
| 750 | 0.7 | 47.8 | 0.4 | 0.2 | 0.6 | 10.2 | 5.1 | 950 | 5143 | 0 |
| 750 | 1.5 | 45.8 | 0.7 | 0.3 | 0.3 | 10.0 | 4.9 | 1070 | 5143 | 20 |
| 750 | 1.9 | 45.7 | 0.9 | 0.3 | 0.3 | 10.0 | 4.9 | 1145 | 5143 | 20 |
| 800 | 5.1 | 49.2 | 2.5 | 0.6 | 0.2 | 10.0 | 4.9 | 1230 | 5143 | 20 |
| 800 | 5.6 | 49.4 | 2.7 | 0.6 | 0.2 | 10.0 | 4.9 | 1305 | 5143 | 20 |
| 800 | 4.3 | 50.0 | 2.2 | 0.6 | 0.2 | 9.9 | 5.2 | 1390 | 5143 | 0 |
| 800 | 4.5 | 50.8 | 2.3 | 0.6 | 0.3 | 9.9 | 5.2 | 1460 | 5143 | 0 |
| 800 | 4.5 | 57.4 | 2.6 | 0.6 | 0.4 | 10.0 | 5.1 | 2390 | 5143 | 0 |
| 800 | 3.8 | 51.3 | 2.0 | 1.0 | 0.1 | 10.5 | 5.0 | 2525 | 5143 | 200 |
| 800 | 4.5 | 52.8 | 2.4 | 1.0 | 0.1 | 10.5 | 5.0 | 2615 | 5143 | 200 |

EXAMPLE 7

(Comparative)

A 5 weight percent hydrated calcium chloride (2.95 weight percent calcium chloride, 1 weight percent calcium) on titanium dioxide catalyst is prepared by the general procedure A set forth above using 0.3 gram of hydrated calcium chloride (6 waters of hydration, from Johnson Matthey/AESAR Group, Seabrook, N.H., Lot number S95049, 99.999 weight percent) and 5.0 grams of titanium dioxide (from Johnson Matthey/AESAR Group, Seabrook, N.H., Lot number S96579, 99.995 weight percent, B.E.T. surface area 0.82 square meter per gram). The catalyst particle size is 30 to 60 mesh (U.S. Sieve Series). The catalyst (5.0 grams) is evaluated in Reactor D, described above, and the results are summarized in Table VIII.

TABLE VIII

| Temp °C. | $CH_4$ C % | Sel % | Yield % | =/− | $CO_2$/CO | $CH_4$ in Mole % | $O_2$ in Mole % | Time Min. | GHSV hr-1 | ECl ppmv |
|---|---|---|---|---|---|---|---|---|---|---|
| 700 | 20.7 | 35.0 | 7.2 | 23.7 | 0.2 | 10.1 | 5.3 | 30 | 1171 | 0 |
| 700 | 22.9 | 21.5 | 4.9 | 5.7 | 0.4 | 10.1 | 5.3 | 110 | 1171 | 0 |
| 700 | 11.6 | 3.4 | 0.4 | 0.4 | 0.6 | 10.1 | 5.0 | 3900 | 1171 | 0 |
| 700 | 21.4 | 17.0 | 3.7 | 3.7 | 0.4 | 10.7 | 5.3 | 4040 | 1171 | 500 |
| 700 | 21.6 | 18.0 | 3.9 | 3.8 | 0.4 | 10.7 | 5.3 | 4125 | 1171 | 500 |
| 700 | 20.5 | 20.5 | 4.3 | 3.9 | 0.4 | 10.7 | 5.3 | 5340 | 1171 | 500 |

EXAMPLE 8

A 6 weight percent hydrated strontium chloride (3.9 weight percent strontium chloride, 2 weight percent strontium) on titanium dioxide catalyst is prepared by the general procedure A set forth above using 0.339 gram of hydrated strontium chloride (6 waters of hydration, from Johnson Matthey/AESAR Group, Seabrook, N.H., Lot number S94313C, 99.9965 weight percent) and 5.00 grams of titanium dioxide (from Johnson Matthey/AESAR Group, Seabrook, N.H., Lot number S96579, 99.995 weight percent, B.E.T. surface area 0.82 square meter per gram). The catalyst particle size is 30 to 60 mesh (U.S. Sieve Series), and 5 grams are used in Reactor D with the equipment and procedures described above. Results are presented in Table IX. A significant increase in the ratio of ethylene to ethane is obtained after addition of 500 ppmv of ethyl chloride to the inlet gas.

TABLE IX

| Temp °C. | $CH_4$ C % | Sel % | Yield % | =/− | $CO_2$/CO | $CH_4$ in Mole % | $O_2$ in Mole % | Time Min. | GHSV hr-1 | ECl ppmv |
|---|---|---|---|---|---|---|---|---|---|---|
| 750 | 38.4 | 32.7 | 12.4 | 22.6 | 0.2 | 10.1 | 5.3 | 60 | 878 | 0 |
| 750 | 36.4 | 27.8 | 9.9 | 17.9 | 0.4 | 10.1 | 5.3 | 145 | 878 | 0 |
| 750 | 26.2 | 7.2 | 1.9 | 1.2 | 0.9 | 10.1 | 5.0 | 3945 | 878 | 0 |
| 750 | 33.8 | 20.6 | 7.1 | 7.5 | 0.6 | 10.7 | 5.3 | 4080 | 878 | 500 |
| 750 | 34.2 | 21.7 | 7.5 | 7.6 | 0.6 | 10.7 | 5.3 | 4170 | 878 | 500 |
| 750 | 32.9 | 23.2 | 7.9 | 7.3 | 0.6 | 10.7 | 5.3 | 5385 | 878 | 500 |

EXAMPLE 9

A 5 weight percent barium carbonate (3.5 weight percent barium) on alpha aluminum oxide catalyst is prepared by the general procedure B set forth above using 0.75 gram of barium carbonate (from Johnson Matthey/AESAR Group, Seabrook, N.H., Lot number S96252B, 99.997 weight percent) and 15 grams of alpha aluminum oxide (from Norton-Company, Akron, Ohio, Sample number 8883118, Type SA 5451, B.E.T. surface area 0.27 square meters per gram). The catalyst particle size is 60 to 100 mesh (U.S. Sieve Series). The performance of the catalyst using the equipment described above is presented in Table X. Reactor D is used with 5.0 grams of catalyst. The addition of 200 ppmv of ethyl chloride at 16975 minutes provided little sustainable increase in ethylene to ethane ratio.

TABLE X

| Temp °C. | $CH_4$ C % | Sel % | Yield % | =/− | $CO_2$/CO | $CH_4$ in Mole % | $O_2$ in Mole % | Time Min. | GHSV hr-1 | ECl ppmv |
|---|---|---|---|---|---|---|---|---|---|---|
| 750 | 38.4 | 33.1 | 12.8 | 2.0 | 7.3 | 9.9 | 4.9 | 60 | 783 | 0 |
| 750 | 37.7 | 31.4 | 11.9 | 1.8 | 7.8 | 9.9 | 4.9 | 140 | 783 | 0 |
| 750 | 36.7 | 31.1 | 11.5 | 1.8 | 7.5 | 9.9 | 4.9 | 240 | 1043 | 0 |
| 750 | 36.4 | 29.9 | 11.0 | 1.7 | 7.8 | 9.9 | 4.9 | 330 | 1043 | 0 |
| 750 | 34.9 | 25.0 | 8.8 | 1.6 | 8.6 | 10.0 | 4.9 | 3975 | 1043 | 0 |
| 750 | 34.1 | 27.2 | 9.3 | 1.4 | 8.6 | 10.0 | 4.9 | 4110 | 2087 | 0 |
| 750 | 34.3 | 26.8 | 9.2 | 1.4 | 8.5 | 10.0 | 4.9 | 4200 | 2087 | 0 |
| 750 | 35.8 | 30.0 | 10.9 | 1.8 | 8.0 | 10.0 | 5.0 | 4290 | 2087 | 30 |
| 750 | 38.0 | 33.9 | 13.0 | 2.1 | 7.4 | 10.0 | 5.0 | 4380 | 2087 | 30 |
| 750 | 39.9 | 48.3 | 19.3 | 2.2 | 2.9 | 9.8 | 4.8 | 5820 | 2087 | 30 |
| 760 | 43.3 | 46.8 | 20.2 | 2.6 | 3.1 | 9.8 | 4.8 | 5895 | 2087 | 30 |
| 760 | 42.8 | 47.1 | 20.2 | 2.5 | 3.0 | 9.8 | 4.8 | 6000 | 2087 | 30 |
| 760 | 42.4 | 47.5 | 20.2 | 2.5 | 3.0 | 9.8 | 4.8 | 6090 | 2087 | 30 |
| 760 | 42.3 | 48.1 | 20.3 | 2.5 | 2.9 | 9.8 | 5.0 | 6225 | 2087 | 30 |
| 760 | 41.7 | 48.7 | 20.3 | 2.4 | 2.9 | 9.8 | 5.0 | 6315 | 2087 | 30 |
| 760 | 41.3 | 49.5 | 20.4 | 2.4 | 2.8 | 9.9 | 5.1 | 6495 | 2087 | 30 |
| 760 | 40.6 | 50.2 | 20.4 | 2.4 | 2.8 | 9.9 | 5.1 | 6675 | 2087 | 30 |
| 760 | 39.6 | 51.7 | 20.5 | 2.3 | 2.7 | 9.9 | 5.1 | 6855 | 2087 | 30 |
| 775 | 45.2 | 49.5 | 22.2 | 3.2 | 2.8 | 9.9 | 4.9 | 6975 | 2087 | 30 |
| 775 | 45.3 | 49.6 | 22.3 | 3.2 | 2.8 | 9.9 | 4.9 | 7005 | 2087 | 30 |
| 775 | 45.3 | 49.7 | 22.4 | 3.3 | 2.7 | 9.9 | 4.9 | 7050 | 2087 | 30 |

TABLE X-continued

| Temp °C. | CH4 C % | Sel % | Yield % | =/- | CO2/CO | CH4 in Mole % | O2 in Mole % | Time Min. | GHSV hr-1 | ECl ppmv |
|---|---|---|---|---|---|---|---|---|---|---|
| 780 | 46.8 | 49.6 | 23.1 | 3.8 | 2.8 | 9.9 | 4.9 | 7095 | 2087 | 30 |
| 780 | 46.8 | 50.0 | 23.3 | 3.9 | 2.6 | 9.9 | 4.9 | 7175 | 2087 | 30 |
| 785 | 48.2 | 50.0 | 24.0 | 4.8 | 2.5 | 9.9 | 4.9 | 7235 | 2087 | 30 |
| 785 | 47.8 | 50.2 | 24.0 | 4.9 | 2.5 | 9.9 | 4.9 | 7265 | 2087 | 30 |
| 790 | 48.9 | 50.4 | 24.6 | 5.8 | 2.3 | 9.9 | 4.9 | 7300 | 2087 | 30 |
| 790 | 49.0 | 50.5 | 24.7 | 6.0 | 2.2 | 9.9 | 4.9 | 7245 | 2087 | 30 |
| 800 | 50.4 | 52.4 | 26.0 | 7.2 | 2.0 | 9.9 | 4.9 | 7395 | 2087 | 30 |
| 800 | 50.0 | 53.2 | 26.1 | 6.8 | 1.9 | 9.9 | 4.9 | 7485 | 2087 | 30 |
| 800 | 47.5 | 50.8 | 23.9 | 5.5 | 2.4 | 10.1 | 5.0 | 8420 | 2087 | 30 |
| 790 | 46.4 | 51.6 | 23.7 | 4.9 | 2.1 | 10.1 | 5.0 | 8455 | 2087 | 30 |
| 790 | 46.3 | 51.8 | 23.8 | 4.9 | 2.1 | 10.1 | 5.0 | 8485 | 2087 | 30 |
| 790 | 46.4 | 51.6 | 23.5 | 4.8 | 1.8 | 10.1 | 5.0 | 8745 | 2087 | 30 |
| 790 | 45.5 | 52.4 | 23.6 | 4.8 | 1.7 | 9.9 | 4.9 | 8790 | 2087 | 40 |
| 790 | 45.6 | 52.2 | 23.6 | 4.9 | 1.5 | 9.9 | 4.9 | 8820 | 2087 | 40 |
| 790 | 44.9 | 52.9 | 23.6 | 4.9 | 1.4 | 9.9 | 4.9 | 8925 | 2087 | 40 |
| 790 | 42.9 | 54.1 | 23.0 | 4.6 | 1.2 | 10.1 | 4.7 | 9735 | 2087 | 40 |
| 800 | 46.1 | 51.8 | 23.5 | 5.1 | 1.4 | 10.0 | 5.0 | 9860 | 2087 | 40 |
| 800 | 46.0 | 51.4 | 23.4 | 5.1 | 1.5 | 10.0 | 5.0 | 9925 | 2087 | 40 |
| 780 | 38.5 | 57.3 | 21.9 | 3.5 | 1.3 | 10.0 | 5.0 | 9960 | 1087 | 40 |
| 760 | 25.4 | 66.9 | 16.8 | 2.0 | 1.1 | 10.0 | 5.0 | 10005 | 2087 | 40 |
| 760 | 23.7 | 67.7 | 15.9 | 2.0 | 1.0 | 10.0 | 5.0 | 10065 | 2087 | 40 |
| 740 | 14.5 | 10.1 | 10.1 | 1.1 | 1.1 | 10.0 | 5.0 | 10095 | 2087 | 40 |
| 740 | 13.3 | 71.0 | 9.4 | 1.0 | 1.0 | 10.0 | 5.0 | 10180 | 2087 | 40 |
| 790 | 41.2 | 56.3 | 22.9 | 4.9 | 0.8 | 10.0 | 5.0 | 10215 | 2087 | 40 |
| 790 | 42.0 | 55.6 | 23.0 | 4.8 | 0.9 | 10.0 | 5.0 | 10245 | 1087 | 40 |
| 790 | 31.8 | 60.1 | 19.0 | 3.2 | 0.7 | 9.9 | 4.7 | 14175 | 2087 | 40 |
| 790 | 31.4 | 59.9 | 18.8 | 3.2 | 0.8 | 10.0 | 4.8 | 14200 | 2087 | 15 |
| 790 | 32.6 | 58.7 | 19.1 | 3.0 | 0.9 | 10.0 | 4.8 | 14265 | 2087 | 15 |
| 790 | 33.7 | 58.1 | 19.5 | 3.1 | 1.0 | 10.0 | 4.8 | 14330 | 2087 | 15 |
| 790 | 34.4 | 57.0 | 19.7 | 3.1 | 1.1 | 9.8 | 4.8 | 14385 | 2087 | 0 |
| 790 | 36.1 | 55.7 | 20.2 | 3.2 | 1.3 | 9.8 | 4.8 | 14450 | 2087 | 0 |
| 790 | 37.1 | 54.5 | 20.5 | 3.3 | 1.6 | 9.8 | 4.8 | 14545 | 2087 | 0 |
| 790 | 37.3 | 53.5 | 20.3 | 3.2 | 1.8 | 9.8 | 4.8 | 14635 | 2087 | 5 |
| 790 | 37.9 | 53.8 | 20.3 | 3.1 | 1.7 | 9.8 | 4.6 | 14725 | 2087 | 5 |
| 790 | 35.1 | 54.0 | 18.9 | 3.1 | 1.2 | 10.0 | 4.8 | 15310 | 2087 | 5 |
| 790 | 38.1 | 52.1 | 19.6 | 3.4 | 1.3 | 10.0 | 4.7 | 15445 | 2087 | 0 |
| 790 | 38.9 | 50.7 | 19.5 | 3.5 | 1.4 | 10.0 | 4.7 | 15535 | 2087 | 0 |
| 790 | 36.0 | 32.8 | 11.8 | 2.2 | 3.6 | 9.9 | 4.8 | 16885 | 2087 | 0 |
| 790 | 32.3 | 39.6 | 12.9 | 2.3 | 2.2 | 10.0 | 4.7 | 16975 | 2087 | 200 |
| 790 | 27.2 | 63.1 | 17.1 | 3.3 | 0.4 | 10.0 | 4.7 | 17065 | 2087 | 200 |
| 790 | 18.3 | 67.1 | 12.2 | 2.5 | 0.3 | 10.0 | 4.7 | 17240 | 2087 | 200 |
| 790 | 24.8 | 64.2 | 15.7 | 3.2 | 0.4 | 9.8 | 4.7 | 17335 | 2087 | 10 |
| 790 | 30.3 | 60.1 | 18.0 | 3.6 | 0.6 | 9.8 | 4.7 | 17425 | 2087 | 10 |
| 790 | 23.0 | 56.7 | 13.0 | 2.2 | 0.7 | 10.0 | 4.8 | 18190 | 2087 | 10 |

EXAMPLE 10

(comparative)

A 1.4 weight percent barium chloride (0.9 weight percent barium) on alpha aluminum oxide catalyst is prepared by the general procedure A set forth above using 0.14 gram of barium chloride (from Johnson Matthey/AESAR Group, Seabrook, N.H., Lot number S94730, 99.9999 weight percent) and 10 grams of alpha aluminum oxide (from Norton-Company, Akron, Ohio, Sample number 83111, Type SA 5551, B.E.T. surface area 0.25 square meter per gram). The catalyst particle size is 60 to 100 mesh (U.S. Sieve Series). The performance of the catalyst using the equipment described above is presented in Table XI. Reactor A is used with 5.0 grams of catalyst.

TABLE XI

| Temp °C. | CH4 C % | Sel % | Yield % | =/- | CO2/CO | CH4 in Mole % | O2 in Mole % | Time Min. | GHSV hr-1 | ECl ppmv |
|---|---|---|---|---|---|---|---|---|---|---|
| 750 | 40.1 | 45.0 | 18.4 | 12.9 | 0.2 | 10.4 | 5.3 | 75 | 1143 | 500 |
| 750 | 39.6 | 41.4 | 16.6 | 13.8 | 0.2 | 10.4 | 5.3 | 165 | 857 | 500 |
| 750 | 38.4 | 41.6 | 16.1 | 14.0 | 0.2 | 10.4 | 5.3 | 255 | 857 | 500 |
| 750 | 37.5 | 41.6 | 15.8 | 13.9 | 0.2 | 10.4 | 5.3 | 345 | 857 | 500 |
| 750 | 35.1 | 43.9 | 15.6 | 10.7 | 0.2 | 10.5 | 5.1 | 1200 | 857 | 500 |
| 750 | 39.9 | 36.6 | 14.9 | 14.5 | 0.2 | 10.5 | 5.1 | 1245 | 571 | 500 |
| 750 | 40.0 | 36.6 | 14.9 | 14.4 | 0.2 | 10.5 | 5.1 | 1290 | 571 | 500 |
| 750 | 38.0 | 41.6 | 16.0 | 12.5 | 0.2 | 10.5 | 5.1 | 1335 | 571 | 500 |
| 750 | 38.0 | 41.7 | 16.1 | 12.4 | 0.2 | 10.5 | 5.1 | 1380 | 571 | 500 |
| 750 | 27.3 | 53.7 | 14.7 | 6.5 | 0.1 | 10.5 | 5.1 | 1425 | 1429 | 500 |
| 750 | 19.8 | 62.3 | 12.4 | 3.8 | 0.1 | 10.5 | 5.1 | 1470 | 2143 | 500 |
| 750 | 28.3 | 54.5 | 15.4 | 6.7 | 0.1 | 10.5 | 5.1 | 1515 | 1143 | 500 |
| 750 | 36.4 | 49.2 | 18.3 | 10.0 | 0.1 | 7.0 | 4.9 | 1605 | 1143 | 500 |
| 750 | 41.7 | 44.1 | 18.8 | 13.0 | 0.1 | 7.0 | 4.9 | 1650 | 857 | 500 |
| 750 | 46.0 | 40.7 | 19.4 | 16.2 | 0.1 | 5.7 | 4.9 | 1740 | 857 | 500 |
| 750 | 38.2 | 47.3 | 18.6 | 10.5 | 0.1 | 5.8 | 5.0 | 2640 | 1143 | 500 |
| 750 | 38.1 | 47.7 | 18.7 | 10.5 | 0.1 | 5.8 | 5.0 | 2685 | 1143 | 500 |
| 775 | 52.9 | 35.3 | 19.7 | 20.0 | 0.2 | 5.8 | 5.0 | 2730 | 1143 | 500 |
| 775 | 47.0 | 41.6 | 20.5 | 14.3 | 0.1 | 5.8 | 5.0 | 2865 | 1714 | 500 |

TABLE XI-continued

| Temp °C. | CH4 C % | Sel % | Yield % | =/− | CO2/CO | CH4 in Mole % | O2 in Mole % | Time Min. | GHSV hr-1 | ECl ppmv |
|---|---|---|---|---|---|---|---|---|---|---|
| 750 | 35.1 | 50.1 | 18.2 | 9.0 | 0.1 | 5.8 | 5.0 | 2905 | 1429 | 500 |
| 775 | 40.0 | 47.8 | 19.9 | 10.5 | 0.1 | 5.8 | 5.0 | 2950 | 2286 | 500 |
| 775 | 39.6 | 48.0 | 19.8 | 10.4 | 0.1 | 5.8 | 5.0 | 2995 | 2286 | 500 |
| 775 | 41.6 | 47.5 | 20.2 | 6.3 | 0.4 | 5.5 | 5.0 | 3080 | 2286 | 100 |
| 775 | 41.9 | 46.9 | 20.1 | 6.3 | 0.5 | 5.5 | 5.0 | 3175 | 2286 | 100 |
| 775 | 42.0 | 47.6 | 20.0 | 6.0 | 0.5 | 5.6 | 5.0 | 3940 | 2286 | 100 |
| 800 | 60.2 | 33.4 | 20.8 | 13.3 | 0.4 | 5.6 | 4.9 | 4075 | 2286 | 100 |
| 750 | 23.8 | 59.3 | 14.0 | 2.6 | 0.5 | 5.6 | 4.9 | 4120 | 2286 | 100 |
| 750 | 37.9 | 47.1 | 17.9 | 5.4 | 0.5 | 5.6 | 4.9 | 4210 | 1143 | 100 |
| 725 | 14.9 | 62.0 | 9.2 | 1.6 | 0.4 | 5.6 | 4.9 | 4250 | 2286 | 100 |
| 725 | 36.3 | 42.6 | 15.5 | 5.4 | 0.5 | 5.6 | 4.9 | 4305 | 571 | 100 |
| 750 | 48.0 | 35.8 | 17.4 | 8.2 | 0.5 | 5.6 | 4.9 | 4350 | 857 | 100 |
| 750 | 35.6 | 42.9 | 15.3 | 5.7 | 0.5 | 9.9 | 5.3 | 4485 | 857 | 100 |

EXAMPLE 11

A 5 weight percent barium chloride (3.5 weight percent barium) on alpha aluminum oxide catalyst is prepared by the general procedure A set forth above using 0.265 gram of barium chloride (from Johnson Matthey/AESAR Group, Seabrook, N.H., Lot number S94730, 99.9999 weight percent) and 5 grams of alpha aluminum oxide (from Norton-Company, Akron, Ohio, Sample number S94730, Type SA 5502, B.E.T. surface area 0.75 square meter per gram). The catalyst particle size is 60 to 100 mesh (U.S. Sieve Series). The performance of the catalyst using the equipment described above is presented in Table XII. Reactor D is used with 5.0 grams of catalyst.

TABLE XII

| Temp °C. | CH4 C % | Sel % | Yield % | =/− | CO2/CO | CH4 in Mole % | O2 in Mole % | Time Min. | GHSV hr-1 | ECl ppmv |
|---|---|---|---|---|---|---|---|---|---|---|
| 750 | 47.8 | 51.7 | 24.3 | 15.1 | 1.5 | 10.2 | 5.2 | 80 | 878 | 10 |
| 750 | 46.5 | 52.6 | 24.3 | 9.8 | 2.5 | 10.2 | 5.2 | 170 | 1171 | 10 |
| 750 | 45.7 | 51.9 | 23.8 | 8.8 | 2.9 | 10.2 | 5.2 | 260 | 1171 | 10 |
| 750 | 36.8 | 45.7 | 16.6 | 3.5 | 1.5 | 10.5 | 5.2 | 2825 | 1171 | 10 |
| 750 | 36.0 | 45.7 | 16.4 | 3.4 | 1.4 | 10.4 | 5.0 | 2915 | 1171 | 30 |
| 750 | 35.1 | 46.5 | 16.2 | 3.3 | 1.2 | 10.4 | 5.0 | 3005 | 1171 | 30 |
| 750 | 29.5 | 45.8 | 13.6 | 3.2 | 0.6 | 10.5 | 5.1 | 6740 | 1171 | 30 |
| 750 | 32.8 | 42.0 | 13.6 | 3.2 | 0.8 | 10.3 | 5.3 | 6875 | 1171 | 0 |
| 750 | 33.8 | 41.9 | 13.9 | 3.1 | 0.9 | 10.3 | 5.3 | 6920 | 1171 | 0 |
| 750 | 34.8 | 40.5 | 13.8 | 3.2 | 1.0 | 10.3 | 5.3 | 7100 | 1171 | 0 |
| 750 | 32.1 | 42.0 | 13.4 | 3.0 | 0.9 | 10.7 | 5.3 | 7190 | 1171 | 200 |
| 750 | 28.1 | 48.2 | 13.6 | 3.9 | 0.2 | 10.7 | 5.3 | 7325 | 1171 | 200 |
| 750 | 31.0 | 49.6 | 15.3 | 5.1 | 0.2 | 10.9 | 5.3 | 7820 | 1171 | 200 |
| 750 | 30.6 | 49.4 | 15.0 | 5.1 | 0.2 | 10.7 | 5.4 | 8315 | 1171 | 200 |
| 750 | 30.7 | 46.4 | 14.2 | 4.3 | 0.3 | 10.4 | 5.4 | 8405 | 1171 | 100 |
| 750 | 30.3 | 46.6 | 14.1 | 4.3 | 0.3 | 10.4 | 5.4 | 8495 | 1171 | 100 |
| 750 | 30.3 | 46.6 | 14.1 | 4.2 | 0.3 | 10.4 | 5.4 | 8585 | 1171 | 100 |
| 750 | 31.8 | 50.3 | 15.9 | 6.3 | 0.1 | 10.9 | 5.2 | 8675 | 1171 | 400 |
| 750 | 32.3 | 49.9 | 16.1 | 6.5 | 0.1 | 10.9 | 5.2 | 8765 | 1171 | 400 |
| 750 | 33.9 | 49.9 | 16.7 | 6.9 | 0.1 | 10.9 | 5.2 | 8990 | 1171 | 400 |
| 750 | 32.9 | 48.9 | 16.1 | 6.9 | 0.1 | 11.2 | 5.2 | 9620 | 1171 | 400 |

EXAMPLE 12

A 8 weight percent hydrated barium bromide (7 weight percent barium bromide, 3.5 weight percent barium) on aluminum oxide catalyst is prepared by the general procedure A set forth above using 0.5 gram of hydrated barium bromide (2 waters of hydration, from Johnson Matthey/AESAR Group, Seabrook, N.H., Lot number S96383, 99.999 weight percent) and 6 grams of aluminum oxide (from Norton Company, Akron, Ohio, Sample number 8883118, Type SA 5451, B.E.T. surface area 0.27 square meter per gram). The catalyst is calcined at 850° C. for 2 hours. The catalyst particle size is 60 to 100 mesh (U.S. Sieve Series). The catalyst is run for 2575 minutes in the absence of added halogen compound. The catalyst is then evaluated for oxidative coupling of methane, using the equipment and procedures described above, and the results are set forth in Table XIII. Ethyl bromide (EBr) is used as the halogen component. Reactor D is used with 5.0 grams of catalyst.

TABLE XIII

| Temp °C. | CH4 C % | Sel % | Yield % | =/− | CO2/CO | CH4 in Mole % | O2 in Mole % | Time Min. | GHSV hr-1 | EBr ppmv |
|---|---|---|---|---|---|---|---|---|---|---|
| 750 | 34.3 | 42.4 | 14.8 | 3.4 | 1.3 | 10.2 | 5.2 | 35 | 2182 | 5 |
| 750 | 33.0 | 47.4 | 15.6 | 3.9 | 1.2 | 10.2 | 5.2 | 110 | 2182 | 5 |
| 750 | 35.7 | 41.0 | 14.5 | 2.9 | 1.5 | 10.5 | 5.1 | 4285 | 2182 | 5 |
| 750 | 36.2 | 40.5 | 14.7 | 3.1 | 1.4 | 9.9 | 5.2 | 4375 | 2182 | 10 |
| 750 | 36.7 | 40.8 | 14.9 | 3.3 | 1.4 | 9.9 | 5.2 | 4510 | 2182 | 10 |
| 750 | 37.3 | 40.5 | 15.1 | 3.5 | 1.4 | 9.8 | 5.1 | 5320 | 2182 | 10 |
| 750 | 37.4 | 40.3 | 15.1 | 3.6 | 1.4 | 9.9 | 5.2 | 5625 | 2182 | 10 |
| 750 | 38.4 | 40.7 | 15.5 | 4.0 | 1.3 | 10.0 | 5.1 | 5725 | 2182 | 17 |
| 750 | 38.5 | 40.3 | 15.5 | 4.1 | 1.3 | 10.0 | 5.1 | 5815 | 2182 | 17 |
| 750 | 38.6 | 40.6 | 15.6 | 4.2 | 1.3 | 10.0 | 5.1 | 5995 | 2182 | 17 |

TABLE XIII-continued

| Temp °C. | CH4 C % | Sel % | Yield % | =/− | CO2/CO | CH4 in Mole % | O2 in Mole % | Time Min. | GHSV hr-1 | EBr ppmv |
|---|---|---|---|---|---|---|---|---|---|---|
| 750 | 37.0 | 40.0 | 14.9 | 3.8 | 1.4 | 10.2 | 5.1 | 6105 | 2182 | 1 |
| 750 | 35.5 | 39.8 | 14.1 | 3.0 | 1.5 | 10.2 | 5.1 | 6220 | 2182 | 1 |

EXAMPLE 13

(Comparative)

A 6 weight percent barium nitrate (3.5 weight percent barium) on alpha aluminum oxide catalyst is prepared by the general procedure B set forth above using 0.40 gram of barium nitrate (from Johnson Matthey/AESAR Group, Seabrook, N.H., Lot number S96252B, 99.997 weight percent) and 6 grams of alpha aluminum oxide (from Norton Company, Akron, Ohio, Sample number 8883118, Type SA 5451, B.E.T. surface area 0.27 square meter per gram). The catalyst is calcined at 850° C. for 4 hours. The catalyst particle size is 60 to 100 mesh (U.S. Sieve Series). The performance of the catalyst using the equipment described above is presented in Table XIV. Reactor D is used with 5.0 grams of catalyst.

EXAMPLE 14

(comparative)

A barium oxide aluminum oxide (barium aluminate) catalyst (available from Alfa, Danvers, Mass., as 3BaO-.Al2O3 (barium aluninate) Lot number K18G, 99.99 weight percent) is calcined at 850° C. for 2 hours. By powder x-ray analysis, the catalyst appears to contain barium oxide, barium carbonate and barium aluminate phases. The performance of 2.0 grams of 60 to 100 mesh (U.S. Sieve Series) catalyst using the equipment and procedures described above, with Reactor D, is presented in Table XV. It can be seen that the highest ethylene to ethane ratios are 2.0 in this example, even with 200 ppmv of ethyl chloride in the inlet gas.

TABLE XIV

| Temp °C. | CH4 C % | Sel % | Yield % | =/− | CO2/CO | CH4 in Mole % | O2 in Mole % | Time Min. | GHSV hr-1 | ECl ppmv |
|---|---|---|---|---|---|---|---|---|---|---|
| 750 | 17.5 | 13.8 | 2.4 | 0.6 | 2.3 | 10.4 | 5.2 | 105 | 2133 | 0 |
| 750 | 17.1 | 13.2 | 2.3 | 0.6 | 2.1 | 10.4 | 5.2 | 330 | 2133 | 0 |
| 750 | 16.2 | 9.1 | 1.5 | 0.6 | 1.9 | 10.4 | 5.3 | 3795 | 2133 | 0 |
| 750 | 26.6 | 52.0 | 14.2 | 3.0 | 0.4 | 10.4 | 5.1 | 3930 | 2133 | 10 |
| 750 | 19.0 | 50.5 | 9.8 | 1.7 | 0.5 | 10.4 | 5.1 | 4020 | 2133 | 10 |
| 750 | 17.7 | 47.8 | 8.5 | 1.5 | 0.5 | 10.4 | 5.1 | 4110 | 2133 | 10 |
| 750 | 14.6 | 38.6 | 5.7 | 1.0 | 0.6 | 10.3 | 5.1 | 4300 | 2133 | 2 |
| 750 | 13.9 | 35.6 | 5.0 | 1.0 | 0.6 | 10.3 | 5.1 | 4380 | 2133 | 2 |
| 750 | 9.4 | 19.6 | 1.9 | 0.5 | 0.6 | 10.3 | 5.1 | 5820 | 2133 | 2 |
| 750 | 12.4 | 27.5 | 3.4 | 0.8 | 0.5 | 10.4 | 5.2 | 5910 | 2133 | 200 |
| 750 | 12.8 | 28.4 | 3.7 | 0.8 | 0.5 | 10.4 | 5.2 | 6000 | 2133 | 200 |
| 750 | 27.5 | 57.5 | 16.0 | 3.3 | 0.3 | 10.3 | 5.2 | 6405 | 2133 | 200 |
| 750 | 26.8 | 57.5 | 15.4 | 3.2 | 0.3 | 10.4 | 5.2 | 6900 | 2133 | 200 |
| 750 | 33.2 | 48.8 | 16.3 | 4.6 | 0.3 | 10.4 | 5.2 | 6935 | 2133 | 200 |
| 750 | 33.3 | 49.6 | 16.5 | 4.5 | 0.3 | 10.4 | 5.2 | 6965 | 2133 | 200 |
| 750 | 25.2 | 56.5 | 14.2 | 3.0 | 0.3 | 10.4 | 5.2 | 7010 | 3000 | 200 |
| 750 | 24.8 | 56.8 | 14.1 | 2.9 | 0.3 | 10.4 | 5.2 | 7050 | 3000 | 200 |
| 750 | 19.6 | 64.1 | 12.5 | 2.1 | 0.3 | 10.4 | 5.2 | 7125 | 3000 | 200 |
| 750 | 19.2 | 65.1 | 12.4 | 2.0 | 0.3 | 10.4 | 5.2 | 7215 | 3000 | 200 |
| 750 | 13.2 | 69.1 | 9.1 | 1.4 | 0.2 | 10.4 | 5.2 | 8340 | 3000 | 200 |
| 750 | 32.1 | 51.0 | 16.4 | 4.6 | 0.2 | 10.4 | 5.2 | 8415 | 1067 | 200 |
| 750 | 31.5 | 51.4 | 16.3 | 4.6 | 0.3 | 10.4 | 5.2 | 8445 | 1067 | 200 |

TABLE XV

| Temp °C. | CH4 C % | Sel % | Yield % | =/− | CO2/CO | CH4 in Mole % | O2 in Mole % | Time Min. | GHSV hr-1 | ECl ppmv |
|---|---|---|---|---|---|---|---|---|---|---|
| 750 | 37.7 | 25.5 | 9.5 | 1.7 | 6.1 | 9.6 | 4.8 | 55 | 3429 | 10 |
| 750 | 39.0 | 28.2 | 10.8 | 1.8 | 6.1 | 9.6 | 4.8 | 155 | 3429 | 10 |
| 750 | 41.9 | 35.6 | 14.7 | 2.0 | 6.3 | 9.2 | 4.6 | 1145 | 3429 | 10 |
| 740 | 41.1 | 33.8 | 13.7 | 2.0 | 5.8 | 9.2 | 4.6 | 1235 | 3429 | 10 |
| 720 | 38.3 | 26.0 | 10.0 | 1.9 | 4.4 | 9.2 | 4.6 | 1325 | 3429 | 10 |
| 700 | 32.6 | 15.8 | 5.2 | 1.4 | 2.6 | 9.2 | 4.6 | 1415 | 3429 | 10 |
| 700 | 32.2 | 15.7 | 5.1 | 1.4 | 2.7 | 9.2 | 4.6 | 1505 | 3429 | 10 |
| 700 | 32.6 | 15.4 | 5.0 | 1.4 | 2.6 | 9.6 | 4.9 | 2405 | 3429 | 10 |
| 700 | 32.6 | 15.3 | 5.0 | 1.4 | 2.6 | 9.5 | 4.8 | 2620 | 3429 | 25 |
| 700 | 32.5 | 14.8 | 4.8 | 1.4 | 2.5 | 9.5 | 4.8 | 2765 | 3429 | 25 |
| 720 | 39.1 | 26.0 | 10.0 | 1.9 | 4.3 | 9.5 | 4.8 | 2840 | 3429 | 25 |
| 720 | 39.2 | 26.2 | 10.1 | 1.9 | 4.3 | 9.5 | 4.8 | 2945 | 3429 | 25 |
| 720 | 39.0 | 26.3 | 10.1 | 1.9 | 4.3 | 9.6 | 4.9 | 3035 | 3429 | 200 |
| 720 | 39.1 | 26.9 | 10.4 | 1.9 | 4.2 | 9.6 | 4.9 | 3530 | 3429 | 200 |
| 720 | 39.2 | 26.9 | 10.4 | 1.9 | 4.2 | 9.6 | 4.9 | 3710 | 3429 | 200 |
| 720 | 38.7 | 26.1 | 10.0 | 1.8 | 3.9 | 9.4 | 4.6 | 4010 | 3429 | 200 |
| 750 | 42.4 | 36.2 | 15.1 | 2.0 | 6.2 | 9.4 | 4.6 | 4070 | 3429 | 200 |
| 750 | 42.6 | 36.6 | 15.3 | 2.0 | 6.2 | 9.4 | 4.6 | 4130 | 3429 | 200 |
| 750 | 42.9 | 36.5 | 15.3 | 2.0 | 5.9 | 9.4 | 4.6 | 4220 | 3429 | 200 |

EXAMPLE 15
(comparative)

A 12 weight percent hydrated strontium chloride (4.5 weight percent strontium) on alpha aluminum oxide catalyst is prepared by the general procedure A set forth above using 2.9 grams of hydrated strontium chloride (6 waters of hydration, from Johnson Matthey/AESAR Group, Seabrook, N.H., Lot number S94313C, 99.9965 weight percent) and 15.00 grams of alpha aluminum oxide (from Norton Company, Akron, Ohio, Sample number 8883118, Type SA 5451, B.E.T. surface area 0.27 square meter per gram). The catalyst is calcined at 850° C. for 4 hours. The catalyst particle size is 60 to 100 mesh (U.S. Sieve Series). The performance of the catalyst using the equipment and procedures described above is presented in Table XVI. Reactor D is used with 5 grams of catalyst.

EXAMPLE 16

A 7 weight percent strontium carbonate (4.5 weight percent strontium) on alpha aluminum oxide catalyst is prepared by the general procedure A set forth above using 1.12 grams of strontium carbonate (from Johnson Matthey/AESAR Group, Seabrook, N.H., Lot number S94313C, 99.99 weight percent) and 15.00 grams of alpha aluminum oxide (from Norton Company, Akron, Ohio, Sample number 8883118, Type SA 5451, B.E.T. surface area 0.27 square meter per gram). The catalyst is calcined at 850° C. for 4 hours. The catalyst particle size is 60 to 100 mesh (U.S. Sieve Series). The performance of the catalyst, using the equipment and procedures described above, with 5 grams of catalyst in Reactor D is presented in Table XVII.

TABLE XVI

| Temp °C. | $CH_4$ C % | Sel % | Yield % | =/− | $CO_2$/CO | $CH_4$ in Mole % | $O_2$ in Mole % | Time Min. | GHSV hr-1 | ECl ppmv |
|---|---|---|---|---|---|---|---|---|---|---|
| 750 | 28.5 | 60.5 | 17.2 | 3.9 | 0.5 | 9.5 | 4.9 | 210 | 1200 | 5 |
| 750 | 29.6 | 62.3 | 18.2 | 4.0 | 0.6 | 9.5 | 4.9 | 340 | 1200 | 5 |
| 750 | 43.3 | 54.1 | 22.8 | 5.4 | 2.2 | 9.5 | 4.9 | 3265 | 1200 | 5 |
| 750 | 23.9 | 60.2 | 14.0 | 1.5 | 2.1 | 9.6 | 4.9 | 7225 | 1200 | 5 |
| 750 | 22.4 | 60.3 | 13.4 | 1.5 | 1.9 | 9.4 | 4.9 | 7495 | 1200 | 50 |
| 750 | 22.5 | 60.6 | 13.4 | 1.5 | 1.9 | 9.4 | 4.9 | 7585 | 1200 | 50 |
| 750 | 19.5 | 64.9 | 12.6 | 1.7 | 1.2 | 9.5 | 4.9 | 9790 | 1200 | 50 |
| 750 | 21.1 | 65.1 | 13.4 | 1.7 | 1.2 | 9.5 | 4.9 | 10040 | 1200 | 50 |
| 750 | 19.1 | 65.5 | 12.4 | 1.6 | 1.2 | 9.5 | 4.9 | 10120 | 1200 | 50 |
| 750 | 20.4 | 65.4 | 13.1 | 1.6 | 1.1 | 9.5 | 4.9 | 10230 | 1200 | 50 |
| 750 | 21.5 | 63.9 | 13.4 | 1.7 | 1.0 | 9.8 | 4.8 | 10310 | 1200 | 500 |
| 750 | 21.2 | 66.5 | 14.0 | 2.1 | 0.8 | 9.8 | 4.8 | 10420 | 1200 | 500 |
| 750 | 19.4 | 65.1 | 12.6 | 3.1 | 0.2 | 9.7 | 4.8 | 12750 | 1200 | 500 |
| 750 | 22.0 | 65.6 | 14.3 | 2.8 | 0.6 | 9.8 | 4.8 | 12850 | 1200 | 5 |
| 750 | 24.0 | 64.7 | 15.3 | 3.0 | 0.7 | 9.8 | 4.8 | 12925 | 1200 | 5 |
| 750 | 24.9 | 63.2 | 15.6 | 3.0 | 0.9 | 9.8 | 4.8 | 13040 | 1200 | 5 |
| 750 | 19.0 | 63.7 | 11.9 | 1.4 | 1.3 | 9.7 | 4.8 | 14105 | 1200 | 5 |
| 750 | 18.4 | 58.2 | 10.5 | 1.3 | 1.0 | 9.8 | 4.8 | 14545 | 1200 | 0 |
| 750 | 17.7 | 58.9 | 10.2 | 1.2 | 1.0 | 9.8 | 4.8 | 14660 | 1200 | 0 |
| 750 | 15.9 | 56.5 | 8.9 | 1.1 | 1.0 | 9.5 | 4.8 | 15425 | 1200 | 0 |
| 750 | 14.6 | 56.2 | 8.2 | 1.1 | 1.0 | 9.6 | 4.8 | 15785 | 1200 | 5 |
| 750 | 15.7 | 55.9 | 8.7 | 1.1 | 1.0 | 9.6 | 4.8 | 16085 | 1200 | 5 |
| 750 | 15.3 | 51.6 | 7.8 | 0.9 | 0.9 | 9.8 | 4.8 | 22745 | 1200 | 5 |

TABLE XVII

| Temp °C. | $CH_4$ C % | Sel % | Yield % | =/− | $CO_2$/CO | $CH_4$ in Mole % | $O_2$ in Mole % | Time Min. | GHSV hr−1 | ECl ppmv |
|---|---|---|---|---|---|---|---|---|---|---|
| 750 | 38.8 | 38.6 | 14.9 | 1.9 | 2.1 | 9.5 | 4.9 | 295 | 2400 | 5 |
| 750 | 38.6 | 39.1 | 15.0 | 1.9 | 2.2 | 9.5 | 4.9 | 385 | 2400 | 5 |
| 750 | 36.0 | 44.1 | 15.6 | 1.8 | 1.5 | 9.7 | 4.9 | 6100 | 2400 | 5 |
| 750 | 34.4 | 45.2 | 15.4 | 1.8 | 1.4 | 9.6 | 4.9 | 7180 | 2400 | 5 |
| 750 | 34.3 | 45.6 | 15.7 | 1.9 | 1.4 | 9.4 | 4.9 | 7450 | 2400 | 50 |
| 750 | 34.9 | 45.8 | 16.0 | 2.0 | 1.3 | 9.4 | 4.9 | 7540 | 2400 | 50 |
| 750 | 34.9 | 50.0 | 17.3 | 2.1 | 1.2 | 9.4 | 4.8 | 8980 | 2400 | 50 |
| 750 | 33.0 | 51.0 | 16.9 | 2.2 | 1.2 | 9.5 | 4.9 | 9745 | 2400 | 50 |
| 750 | 31.8 | 53.1 | 16.8 | 1.9 | 1.2 | 9.5 | 4.9 | 10005 | 2400 | 50 |
| 750 | 30.9 | 54.2 | 16.8 | 1.9 | 1.3 | 9.5 | 4.9 | 10080 | 2400 | 50 |
| 750 | 32.1 | 55.8 | 17.6 | 1.9 | 1.3 | 9.5 | 4.9 | 10285 | 2400 | 50 |
| 750 | 30.3 | 56.0 | 17.1 | 1.9 | 1.4 | 9.8 | 4.8 | 10375 | 2400 | 500 |
| 750 | 27.8 | 59.0 | 16.4 | 1.8 | 1.5 | 9.8 | 4.8 | 10465 | 2400 | 500 |
| 750 | 17.2 | 74.7 | 12.6 | 2.0 | 0.4 | 9.9 | 4.8 | 12625 | 2400 | 500 |
| 750 | 16.9 | 76.7 | 12.8 | 1.8 | 0.6 | 9.8 | 4.8 | 12795 | 2400 | 5 |
| 750 | 20.3 | 74.2 | 14.9 | 2.1 | 0.8 | 9.8 | 4.8 | 12890 | 2400 | 5 |
| 750 | 20.8 | 72.3 | 14.9 | 2.0 | 0.9 | 9.8 | 4.8 | 12950 | 2400 | 5 |
| 750 | 18.5 | 65.8 | 12.1 | 1.2 | 1.0 | 9.7 | 4.8 | 14060 | 2400 | 5 |
| 750 | 18.5 | 60.3 | 10.9 | 1.0 | 0.8 | 9.8 | 4.8 | 14600 | 2400 | 0 |
| 750 | 18.2 | 59.1 | 10.6 | 1.0 | 0.8 | 9.8 | 4.8 | 14735 | 2400 | 0 |
| 750 | 17.0 | 54.1 | 9.2 | 0.9 | 0.7 | 9.5 | 4.8 | 15500 | 2400 | 0 |
| 750 | 16.8 | 54.6 | 9.2 | 0.9 | 0.7 | 9.6 | 4.8 | 15745 | 2400 | 5 |
| 750 | 17.1 | 54.1 | 9.3 | 0.9 | 0.7 | 9.6 | 4.8 | 16045 | 2400 | 5 |
| 750 | 16.8 | 53.4 | 8.9 | 0.8 | 0.6 | 9.8 | 4.8 | 22700 | 2400 | 5 |

EXAMPLE 17

Table XIX. Reactor D is used with 5 grams of catalyst.

TABLE XIX

| Temp °C. | CH$_4$ C % | Sel % | Yield % | =/− | CO$_2$/CO | CH$_4$ in Mole % | O$_2$ in Mole % | Time Min. | GHSV hr$^{-1}$ | ECl ppmv |
|---|---|---|---|---|---|---|---|---|---|---|
| 750 | 38.4 | 32.7 | 12.4 | 22.6 | 0.2 | 10.1 | 5.3 | 60 | 878 | 0 |
| 750 | 36.4 | 27.8 | 9.9 | 17.9 | 0.4 | 10.1 | 5.3 | 145 | 878 | 0 |
| 750 | 26.2 | 7.2 | 1.9 | 1.2 | 0.9 | 10.1 | 5.0 | 3945 | 878 | 0 |
| 750 | 33.8 | 20.6 | 7.1 | 7.5 | 0.6 | 10.7 | 5.3 | 4080 | 878 | 500 |
| 750 | 34.2 | 21.7 | 7.5 | 7.6 | 0.6 | 10.7 | 5.3 | 4170 | 878 | 500 |
| 750 | 32.9 | 23.2 | 7.9 | 7.3 | 0.6 | 10.7 | 5.3 | 5385 | 878 | 500 |

(Comparative)

A 12 weight percent zinc chloride on alpha aluminum oxide catalyst is prepared by the general procedure A set forth above using 0.18 gram of zinc chloride (Baker Analyzed Reagent, Lot number 41533, 99 weight percent) and 5 grams of alpha aluminum oxide (from Norton Company, Akron, Ohio, Sample number 83111, Type SA 5551, B.E.T. surface area 0.25 square meter per gram). The catalyst particle size is 30 to 60 mesh (U.S. Sieve Series). The performance of the catalyst using the equipment described above is presented in Table XVIII. Reactor C is used with 5 grams of catalyst.

TABLE XVIII

| Temp °C. | CH$_4$ C % | Sel % | Yield % | =/− | CO$_2$/CO | CH$_4$ in Mole % | O$_2$ in Mole % | Time Min. | GHSV hr$^{-1}$ | ECl ppmv |
|---|---|---|---|---|---|---|---|---|---|---|
| 750 | 23.3 | 46.6 | 10.5 | 2.5 | 1.8 | 10.0 | 5.4 | 45 | 878 | 0 |
| 750 | 19.9 | 45.8 | 8.8 | 1.7 | 1.2 | 10.0 | 5.4 | 150 | 878 | 0 |
| 750 | 15.8 | 41.8 | 6.7 | 1.6 | 0.9 | 10.0 | 4.9 | 1005 | 878 | 0 |
| 750 | 19.5 | 48.5 | 9.4 | 2.4 | 1.2 | 10.1 | 4.7 | 1185 | 878 | 50 |
| 750 | 20.3 | 47.6 | 9.6 | 2.6 | 1.2 | 10.1 | 4.7 | 1275 | 878 | 50 |
| 750 | 21.3 | 48.4 | 10.3 | 2.5 | 0.7 | 10.3 | 5.1 | 3885 | 878 | 50 |
| 750 | 26.3 | 50.1 | 13.4 | 5.9 | 0.3 | 10.5 | 4.8 | 4060 | 878 | 500 |
| 750 | 25.8 | 49.8 | 13.1 | 5.8 | 0.2 | 10.5 | 4.8 | 4140 | 878 | 500 |
| 750 | 24.8 | 46.5 | 11.7 | 6.2 | 0.1 | 10.5 | 4.8 | 4325 | 878 | 500 |
| 750 | 20.1 | 49.4 | 9.9 | 2.8 | 0.3 | 10.4 | 5.4 | 4470 | 878 | 100 |
| 750 | 19.8 | 49.8 | 9.9 | 2.7 | 0.3 | 10.4 | 5.1 | 4605 | 878 | 100 |
| 750 | 15.5 | 46.2 | 7.2 | 2.4 | 0.2 | 10.4 | 4.9 | 8025 | 878 | 100 |
| 750 | 16.5 | 45.4 | 7.4 | 2.1 | 0.2 | 10.3 | 5.0 | 8340 | 878 | 50 |
| 750 | 16.9 | 44.9 | 7.5 | 2.1 | 0.2 | 10.3 | 5.0 | 8435 | 878 | 50 |

EXAMPLE 18

(comparative)

Titanium dioxide (from Johnson Matthey/AESAR Group, Seabrook, N.H., Lot number S96579, 99.995 weight percent, B.E.T. surface area 0.82 square meter per gram, 30 to 60 mesh, U.S. Sieve Series) is tested as catalyst for methane coupling using the equipment and procedures described above. Results are presented in

EXAMPLE 19

(Comparative)

Zirconium dioxide (from Johnson Matthey/AESAR Group, Seabrook, N.H., Lot number S96307, 99.9975 weight percent, B.E.T. surface area 0.95 square meter per gram, 30 to 60 mesh, U. S. Sieve Series) is tested as catalyst for methane coupling using the equipment and procedures described above. Results are presented in Table XX. Reactor D is used with 5 grams of catalyst.

TABLE XX

| Temp °C. | CH$_4$ C % | Sel % | Yield % | =/− | CO$_2$/CO | CH$_4$ in Mole % | O$_2$ in Mole % | Time Min. | GHSV hr$^{-1}$ | ECl ppmv |
|---|---|---|---|---|---|---|---|---|---|---|
| 700 | 32.8 | 1.1 | 0.3 | 0.8 | 1.4 | 9.6 | 4.7 | 55 | 1000 | 50 |
| 700 | 31.4 | 1.0 | 0.3 | 0.8 | 0.9 | 9.6 | 4.7 | 130 | 2000 | 50 |
| 750 | 34.0 | 2.4 | 0.8 | 1.0 | 1.3 | 9.6 | 4.7 | 360 | 2000 | 50 |
| 750 | 32.1 | 2.5 | 0.8 | 0.9 | 1.0 | 9.6 | 4.8 | 435 | 3200 | 50 |
| 800 | 32.4 | 6.8 | 2.3 | 1.3 | 1.2 | 9.3 | 4.9 | 1440 | 3200 | 50 |

EXAMPLE 20

(comparative)

Gallium oxide (from Johnson Matthey/AESAR Group, Seabrook, N.H., Lot number S70392, 99.999 weight percent, B.E.T. surface area 4.22 square meters per gram, 30 to 60 mesh, U.S. Sieve Series) is tested as catalyst for methane coupling using the equipment and procedures described above. Results are presented in Table XXI. A dash is shown when ethane amounts are too small for accurate ratios to be ascertained. Reactor D is used with 5 grams of catalyst.

TABLE XXI

| Temp °C. | CH$_4$ C % | Sel % | Yield % | =/− | CO$_2$/CO | CH$_4$ in Mole % | O$_2$ in Mole % | Time Min. | GHSV hr$^{-1}$ | ECl ppmv |
|---|---|---|---|---|---|---|---|---|---|---|
| 700 | 25.8 | 0.0 | 0.0 | 130.1 | 60.3 | 10.0 | 5.1 | 40 | 900 | 0 |
| 700 | 26.5 | 0.0 | 0.0 | — | 42.9 | 10.0 | 5.1 | 125 | 2400 | 0 |
| 650 | 27.1 | 0.9 | 0.2 | 6.4 | 32.0 | 10.0 | 5.1 | 205 | 2400 | 0 |

TABLE XXI-continued

| Temp °C. | CH4 C % | Sel % | Yield % | =/− | CO2/CO | CH4 in Mole % | O2 in Mole % | Time Min. | GHSV hr⁻¹ | ECl ppmv |
|---|---|---|---|---|---|---|---|---|---|---|
| 650 | 27.4 | 0.8 | 0.2 | 8.6 | 31.2 | 10.0 | 5.1 | 290 | 2400 | 0 |
| 600 | 27.6 | 1.8 | 0.5 | 1.2 | 8.9 | 10.0 | 5.1 | 365 | 2400 | 0 |
| 550 | 27.2 | 1.0 | 0.3 | 0.6 | 4.8 | 10.0 | 5.1 | 425 | 2400 | 0 |
| 550 | 27.1 | 1.0 | 0.3 | 0.5 | 4.8 | 10.0 | 5.1 | 465 | 2400 | 0 |
| 550 | 22.6 | 0.1 | 0.0 | — | 2.6 | 10.2 | 5.4 | 600 | 2400 | 50 |
| 550 | 23.6 | 0.1 | 0.0 | — | 2.7 | 10.2 | 5.4 | 690 | 2400 | 50 |
| 550 | 21.3 | 0.1 | 0.0 | — | 2.7 | 10.0 | 5.2 | 1320 | 2400 | 50 |
| 550 | 24.5 | 0.4 | 0.1 | 1.0 | 4.4 | 10.1 | 5.3 | 1460 | 2400 | 0 |
| 550 | 25.8 | 0.5 | 0.1 | 1.1 | 5.1 | 10.1 | 5.3 | 1525 | 2400 | 0 |
| 550 | 25.8 | 0.5 | 0.1 | 0.8 | 5.4 | 10.1 | 5.3 | 1600 | 2400 | 0 |

EXAMPLES 21 To 23

The following catalysts are prepared using the general procedures given below.

Procedure A: The selected alkaline earth metal component is dissolved in just enough deionized water at room temperature to wet the alpha-alumina support (The Norton Company, Akron, Ohio, SA-5402 30–60 mesh used for all catalysts). The alpha-alumina support is added to the solution and mixed to assure total uptake of the liquid and uniform impregnation of the alumina by incipient wetness. The alkaline earth metal component and alumina support are provided in relative amounts to each other to provide the desired loading of alkaline earth metal component on the catalyst. The material is then dried in a vacuum oven at about 110° to 130 °C. Drying is usually complete in 4 to 6 hours; however drying overnight does not appear to affect performance. The catalyst is tested without further treatment.

Procedure B: The selected insoluble alkaline earth metal component and the alpha-alumina support are added to 50 to 100 milliliters of deionized water at room temperature. The alkaline earth metal component and alpha-alumina support are provided in relative amounts to each other to provide the desired loading of alkaline earth metal component on the catalyst. The mixture is constantly stirred at about 80° to 90 °C. until a thick paste remains. The paste is then dried in a vacuum oven at about 110° to 130 °C. Drying is usually complete in 4 to 6 hours; however drying overnight does not appear to affect performance. The catalyst is tested without further treatment.

Procedure C: The selected metal component is dissolved in just enough deionized water at room temperature to wet the alkaline earth metal component/alpha-alumina catalyst prepared using procedure A or B. In the event that the metal component is not sufficiently soluble to form a solution, concentrated hydrochloric acid is added dropwise until the component dissolves. The alkaline earth metal component/alpha-alumina catalyst is added to the solution and mixed to assure total uptake of the liquid and uniform impregnation of the alumina by incipient wetness. The metal component and alkaline earth metal component/alpha-alumina catalyst are provided in relative amounts to each other to provide the desired loading of metal component on the catalyst. The material is then dried in a vacuum oven at about 110° to 130 °C. Drying is usually complete in 4 to 6 hours; however drying overnight does not appear to affect performance. The catalyst is tested without further treatment.

TABLE XXII

| Catalyst | Procedure | Dopant | Wt. % Based on Total Catalyst | Base Catalyst |
|---|---|---|---|---|
| B | A & C | Co(NO3)2 | 0.82 | 6.2 wt. % SrCl2/alumina |
| H | B & C | Co(NO3)2 | 0.82 | 5.8 wt. % SrCO3/alumina |

The following examples are conducted using the equipment described below. A quartz reactor is used which comprises a 1.5 centimeter (inside diameter) quartz tube about 55.9 centimeters in length with quartz "O"-ring joints at each end. At the bottom, a quartz effluent tube extends radially outward. Axially within the reactor tube is another quartz tube (1.3 centimeters outside diameter (1.1 centimeters inside diameter)) extending from the bottom (effluent end) of the reactor for about 28 centimeters. This tube is terminated with a joined 5 centimeters tube axially positioned thereon having an outside diameter of 0.5 centimeter and inside diameter of 0.3 centimeter. The annular region around this thinner tube ("annular reactor portion") receives the catalyst. These inner tubes form a thermocouple well. The thermocouple well extends 33 centimeters into the reactor from the bottom of the tube. The reactor is encased in a Lindberg oven for the mid-31 centimeters of its length. The incoming and exiting lines from the reactor are capable of being sampled by gas chromatography.

The catalyst bed is formed in the reactor by providing 20 to 40 mesh (U.S. Sieve Series) quartz chips around the larger diameter section of the thermocouple well, placing quartz wool over the chips (1 centimeter), forming the bed of catalysts (3 to 5 grams) wherein the catalyst particles have an average size of about 250 to 600 microns and then placing glass wool over the catalyst (1 centimeter) and either more quartz chips on the glass wool or a combination of an axially extending 1.3 centimeters outside diameter quartz solid rod with the quartz chips in the annular zone around the solid rod, to fill the upper portion of the reactor tube.

In the general operating procedure, the reactor is flushed with nitrogen while heating to about reaction temperature. The reactant stream is fed and the reactor is brought to the desired temperature. Periodic analyses of the gases are conducted (usually at intervals between one and two hours). The reactor pressure is about 5 pounds per square inch gauge (135 kPa absolute) and the feed usually contains $CH_4/O_2/N_2$ in a mole ratio of about 2/1/20. In the following Tables =/− designates the ethylene to ethane mole ratio, and time is the time that the catalyst is on stream. "CH4 Conv." is the total percent of methane reacted based on the amount of methane in the product gas. "$C_2$ Sel." is the mole percent of carbon converted to ethylene and ethane compared to the total moles of carbon in the observed products. "$C_3$Sel." is the mole percent of carbon converted to propylene and propane "$C_2$ yield" is the $CH_4$ Conv. times $C_2$ Sel./100. The gas hourly space velocity is based on the volumetric flow rate of the feed at ambient temperature and pressure per volume of the reactor occupied by the catalyst.

EXAMPLE 21

(Comparative)

The performance of catalyst B using the equipment and procedures described previously is presented in Tables XXIII and XXIV. Reactant feed gas ratio of $CH_4/O_2/N_2$ is 2.2/1/20.

TABLE XXIII

| Temp. °C. | $CH_4$ Conv. % | $C_2$ Sel. % | $C_3$ Sel. % | $C_2$ Yield % | =/— Ratio molar | Time Hr. | GHSV $Hr^{-1}$ |
|---|---|---|---|---|---|---|---|
| 650 | 33 | 65 | 3.3 | 20.7 | 5.2 | 1 | 1500 |
| 650 | 24 | 66 | 3.2 | 15.4 | 2.3 | 3 | 1500 |
| 650 | 21 | 67 | 3.2 | 13.7 | 1.9 | 11 | 1500 |
| 650 | 20 | 68 | 3.8 | 13.2 | 1.7 | 19 | 1500 |
| 670 | 29 | 69 | 3.9 | 18.8 | 3.0 | 21 | 1500 |
| 670 | 25 | 69 | 3.8 | 16.9 | 3.0 | 23 | 1500 |
| 670 | 22 | 67 | 3.0 | 14.1 | 1.7 | 31 | 1500 |
| 670 | 20 | 56 | 2.9 | 10.6 | 1.2 | 35 | 1500 |

TABLE XXIV

| Temp. °C. | $CH_4$ Conv. % | $C_2$ Sel. % | $C_3$ Sel. % | $C_2$ Yield % | =/— Ratio molar | Time Hr. | GHSV $Hr^{-1}$ |
|---|---|---|---|---|---|---|---|
| 600 | 17 | 44 | 1.3 | 7.7 | 2.4 | 1 | 612 |
| 600 | 13 | 44 | — | 6.1 | 1.5 | 3 | 612 |
| 600 | 11 | 45 | 1.0 | 4.9 | 1.4 | 7 | 612 |
| 625 | 20 | 56 | 2.3 | 11.6 | 2.5 | 9 | 612 |
| 625 | 19 | 56 | 2.2 | 10.6 | 2.2 | 13 | 612 |
| 625 | 16 | 58 | 2.1 | 9.6 | 1.8 | 21 | 612 |
| 650 | 27 | 61 | 3.2 | 17.5 | 4.1 | 23 | 612 |
| 650 | 29 | 65 | 3.1 | 19.5 | 4.5 | 27 | 612 |
| 650 | 27 | 64 | 4.8 | 17.9 | 3.5 | 33 | 612 |
| 650 | 24 | 67 | 3.2 | 16.2 | 3.0 | 45 | 612 |

EXAMPLE 22

(Comparative)

The performance of catalyst H using the equipment and procedures described previously is presented in Table XXIV. Reactant feed gas ratio of $CH_4/O_2/N_2$ is 2.2/1/20. No ethyl chloride is added.

TABLE XXV

| Temp. °C. | $CH_4$ Conv. % | $C_2$ Sel. % | $C_3$ Sel. % | $C_2$ Yield % | =/— Ratio molar | Time Hr. | GHSV $Hr^{-1}$ |
|---|---|---|---|---|---|---|---|
| 600 | 20 | 3.4 | 0.0 | 0.7 | 0.8 | 3 | 714 |
| 600 | 16 | 0.5 | 0.0 | 0.1 | 0.7 | 9 | 714 |
| 625 | 20 | 3.2 | 0.0 | 0.7 | 0.9 | 17 | 714 |
| 625 | 21 | 2.7 | 0.0 | 0.6 | 0.8 | 21 | 714 |
| 650 | 22 | 2.8 | 0.0 | 0.6 | 0.9 | 23 | 714 |
| 650 | 22 | 0.6 | 0.0 | 0.1 | 0.4 | 39 | 714 |

EXAMPLE 22

The performance of catalyst H using the equipment and procedures described previously is presented in Table XXVI. The results show the effect of ethyl chloride (ECl) in the feed stream on catalyst H. Reactant feed gas ratio of $CH_4/O_2/N_2$ is 2.2/1/20 with an ethyl chloride concentration of 100 ppm.

TABLE XXVI

| Temp. °C. | $CH_4$ Conv. % | $C_2$ Sel. % | $C_3$ Sel. % | $C_2$ Yield % | =/— Ratio molar | Time Hr. | GHSV $Hr^{-1}$ |
|---|---|---|---|---|---|---|---|
| 650 | 13 | 8.5 | 0.0 | 1.1 | 0.7 | 1 | 880 |
| 650 | 13 | 12 | 0.0 | 1.6 | 0.8 | 5 | 880 |
| 650 | 12 | 18 | 0.2 | 2.2 | 0.9 | 13 | 880 |
| 650 | 12 | 25 | 0.4 | 3.0 | 1.1 | 17 | 880 |
| 700 | 23 | 54 | 2.3 | 12.5 | 2.0 | 21 | 880 |
| 700 | 18 | 51 | 3.3 | 9.5 | 1.7 | 27 | 880 |
| 700 | 14 | 43 | 1.3 | 6.4 | 1.6 | 39 | 880 |
| 650 | 6.0 | 37 | 0.9 | 2.3 | 1.0 | 43 | 880 |
| 650 | 6.1 | 39 | 0.7 | 2.4 | 1.0 | 51 | 880 |

It is claimed:

1. A process for oxidative coupling of alkane comprising methane to heavier hydrocarbons comprising ethane and ethylene, comprising feeding the alkane, reactive oxygen-containing material and halogen-containing vapor phase additive to a reaction zone containing a catalytically effective amount of oxidative coupling catalyst said oxidative coupling catalyst comprising at least one catalytically active barium and/or strontium compound and metal oxide combustion promoter comprising at least one Group IVA or Group IIIB metal oxide and other than a silica combustion promoter; maintaining the reaction zone under oxidative coupling conditions to convert at least a portion of the methane to ethylene and ethane, and withdrawing from the reaction zone an effluent containing ethylene and ethane produced in the reaction zone, wherein the metal oxide and halogen-containing vapor phase additive are provided in amounts sufficient to provide an ethylene to ethane mole ratio in the effluent of at least about 2.5.

2. The process of claim 1 wherein the metal oxide combustion promoter converts at least about 5 per cent of methane under Oxidation Conditions to carbon oxides.

3. The process of claim 2 wherein the metal oxide combustion promoter comprises at least one of titanium dioxide, zirconium dioxide, aluminum oxide and gallium oxide.

4. The process of claim 1 wherein the metal oxide combustion promoter comprises at least one of titanium dioxide, zirconium dioxide, aluminum oxide and gallium oxide.

5. The process of claim 2 wherein at least one barium and/or strontium compound comprises at least one of oxide, peroxide, hydroxide, carbonate, chloride, bromide and iodide.

6. The process of claim 2 wherein sufficient barium and strontium compound is present to provide a yield of higher hydrocarbon based on alkane fed of at least 15 mole percent under Standard Reference Conditions.

7. The process of claim 2 wherein barium and/or strontium compound comprises 1 to 20 weight percent of the catalyst.

8. The process of claim 2 wherein the catalyst is a supported catalyst.

9. The process of claim 8 wherein the support comprises metal oxide combustion promoter.

10. The Process of claim 9 wherein the support comprises at least one of titanium dioxide, zirconium oxide, aluminum oxide and gallium oxide.

11. The process of claim 10 wherein the support has a surface area of at least about 0.2 square meter per gram.

12. The process of claim 2 wherein the metal oxide combustion promoter comprises alpha aluminum oxide having a surface acidity of at least about 1.25 micromoles of acid sites per square meter of surface area.

13. The process of claim 2 wherein the halogen-containing vapor phase additive comprises at least one of hydrogen halide, organic halide of 1 to 3 carbon atoms and halogen, wherein the halide or halogen is at least one of chlorine, bromine and iodine.

14. The process of claim 13 wherein the halogen-containing vapor phase additive is provided in an amount of about 10 to 1000 ppmv based on the feed to the reactor zone.

15. The process of claim 14 wherein the halogen-containing vapor phase additive is provided in an amount sufficient to provide an ethylene to ethane mole ratio in the effluent of at least about 3.

16. The process of claim 14 wherein the weight ratio of barium and/or strontium compound to metal oxide combustion promoter is between about 0.05:10 to 20:1.

17. The process of claim 2 wherein the reactive oxygen-containing material comprises oxygen.

18. The process of claim 2 wherein the oxidative coupling conditions comprise a temperature between about 600° C. and 800° C., a pressure of about 1 to 50 atmospheres absolute, a gas hourly space velocity of between about 500 and 15000 reciprocal hours, and a mole ratio of alkane to active oxygen atom of the reactive oxygen-containing material of about 1:1 to 20:1.

19. A process for oxidative coupling of alkane comprising methane to heavier hydrocarbon comprising ethane and ethylene, comprising feeding the alkane, reactive oxygen-containing material and halogen-containing vapor phase additive to a reaction zone containing a catalytically effective amount of oxidative coupling catalyst, said oxidative coupling catalyst comprising at least one catalytically active barium and/or strontium compound and at least one metal oxide selected from the group consisting of titanium dioxide, zirconium dioxide and gallium oxide wherein barium and/or strontium compound is provided in an amount sufficient to reduce combustion to carbon oxides; maintaining the reactive zone under oxidative coupling conditions to convert at least a portion of the methane to ethylene and ethane; and withdrawing from the reacton an effluent containing ethylene and ethane produced in the reacton zone, wherein the metal oxide and halogen-containing vapor phase additive are provided in amounts sufficient to provide an ethylene to ethane mole ratio in the effluent of at least about 2.5.

20. The process of claim 19 wherein the catalyst is a supported catalyst and the reactive oxygen-containing material comprises oxygen.

21. The process of claim 20 wherein the support comprises said metal oxide.

22. The process of claim 21 wherein the weight ratio of barium and/or strontium compound to metal oxide is between about 0.05:10 to 20:1.

23. The process of claim 22 wherein the halogen-containing vapor phase additive comprises at least one of hydrogen halide, organic halide of 1 to 3 carbon atoms and halogen, wherein the halide or halogen is at least one of chlorine, bromine and iodine.

24. The process of claim 23 wherein the halogen-containing vapor phase additive is provided in an amount of about 10 to 1000 ppm based on the feed to the reaction zone.

25. The process of claim 24 wherein the halogen-containing vapor phase additive is provided in an amount sufficient to provide an ethylene to ethane mole ratio in the effluent of at least about 3.

26. The process of claim 25 wherein the oxidative coupling conditions comprise a temperature between about 600° and 800° C. and a gas hourly space velocity of between about 500 and 15000 reciprocal hours.

27. The process of claim 26 wherein the mole ratio of alkane to oxygen atom is about 1:1 to 20:1.

28. The process of claim 27 wherein sufficient barium and strontium compound is present to provide a yield of higher hydrocarbons based on alkane in the feed of at least 15 weight percent under Standard Reference Conditions.

29. The process of claim 28 wherein the support comprises titanium dioxide.

* * * * *